(12) United States Patent
Jian et al.

(10) Patent No.: US 8,946,417 B2
(45) Date of Patent: Feb. 3, 2015

(54) SYNTHESIS OF FOUR COORDINATED PLATINUM COMPLEXES AND THEIR APPLICATIONS IN LIGHT EMITTING DEVICES THEREOF

(75) Inventors: Li Jian, Phoenix, AZ (US); Zixing Wang, Shanghai (CN); Eric Turner, Phoenix, AZ (US)

(73) Assignee: Arizona Board Of Regents Acting For And On Behalf Of Arizona State University, Scottsdale, AZ (US)

( * ) Notice: Subject to any disclaimer, the term of this patent is extended or adjusted under 35 U.S.C. 154(b) by 10 days.

(21) Appl. No.: 13/263,096

(22) PCT Filed: Apr. 6, 2010

(86) PCT No.: PCT/US2010/030095
§ 371 (c)(1),
(2), (4) Date: Jan. 3, 2012

(87) PCT Pub. No.: WO2010/118026
PCT Pub. Date: Oct. 14, 2010

(65) Prior Publication Data
US 2012/0095232 A1    Apr. 19, 2012

Related U.S. Application Data

(60) Provisional application No. 61/166,901, filed on Apr. 6, 2009.

(51) Int. Cl.
| | | |
|---|---|---|
| C07F 15/00 | (2006.01) | |
| C09K 11/06 | (2006.01) | |
| H01L 51/00 | (2006.01) | |
| H05B 33/14 | (2006.01) | |
| H01L 51/50 | (2006.01) | |

(52) U.S. Cl.
CPC .............. *C07F 15/0086* (2013.01); *C09K 11/06* (2013.01); *H01L 51/0087* (2013.01); *H05B 33/14* (2013.01); *C09K 2211/1007* (2013.01); *C09K 2211/1014* (2013.01); *C09K 2211/1029* (2013.01); *C09K 2211/1044* (2013.01); *C09K 2211/185* (2013.01); *H01L 51/5016* (2013.01); *Y02E 10/549* (2013.01)
USPC ............................................. 546/2; 548/101

(58) Field of Classification Search
USPC .................. 546/2; 548/101; 313/504
See application file for complete search history.

(56) References Cited

U.S. PATENT DOCUMENTS

| | | | |
|---|---|---|---|
| 6,780,528 | B2 | 8/2004 | Tsuboyama et al. |
| 7,501,190 | B2 | 3/2009 | Ise |
| 7,947,383 | B2 * | 5/2011 | Ise et al. ............ 428/690 |
| 2002/0068190 | A1 | 6/2002 | Tsuboyama et al. |
| 2006/0202197 | A1 | 9/2006 | Nakayama et al. |
| 2006/0210831 | A1 | 9/2006 | Sano et al. |
| 2006/0263635 | A1 | 11/2006 | Ise |
| 2007/0057630 | A1 | 3/2007 | Nishita et al. |
| 2007/0059551 | A1 | 3/2007 | Yamazaki |
| 2008/0001530 | A1 | 1/2008 | Ise et al. |
| 2008/0054799 | A1 | 3/2008 | Satou |
| 2008/0079358 | A1 | 4/2008 | Satou |
| 2008/0241518 | A1 | 10/2008 | Satou et al. |
| 2008/0241589 | A1 | 10/2008 | Fukunaga et al. |
| 2009/0026936 | A1 | 1/2009 | Satou et al. |
| 2009/0026939 | A1 | 1/2009 | Kinoshita et al. |
| 2009/0032989 | A1 | 2/2009 | Karim et al. |
| 2009/0039768 | A1 | 2/2009 | Igarashi et al. |
| 2009/0128008 | A1 | 5/2009 | Ise et al. |
| 2009/0261721 | A1 | 10/2009 | Murakami et al. |

FOREIGN PATENT DOCUMENTS

| | | |
|---|---|---|
| CN | 101142223 A | 3/2008 |
| EP | 1808052 A1 | 7/2007 |
| EP | 1874893 A1 | 1/2008 |
| EP | 1874894 A1 | 1/2008 |
| EP | 1919928 A1 | 5/2008 |
| EP | 2096690 A2 | 9/2009 |
| EP | 2112213 B1 | 7/2012 |
| JP | 2005-267557 A | 9/2005 |
| JP | 2005-310733 A | 11/2005 |
| JP | 2006-047240 A | 2/2006 |
| JP | 2006-232784 A | 9/2006 |
| JP | 2006-242080 A | 9/2006 |
| JP | 2006-242081 A | 9/2006 |
| JP | 2006-256999 A | 9/2006 |
| JP | 2006-257238 A | 9/2006 |
| JP | 2006-261623 A | 9/2006 |
| JP | 2006-313796 A | 11/2006 |
| JP | 2006-332622 A | 12/2006 |
| JP | 2006-351638 A | 12/2006 |
| JP | 2007-019462 A | 1/2007 |

(Continued)

OTHER PUBLICATIONS

First Office Action issued on Jun. 26, 2013 by the Chinese patent Office for Application No. 201080024040.X filed Apr. 6, 2010 (Applicant—Arizona Board of Regents / Inventors—Jian Li, et al.) (pp. 1-16).

Official Communication issued by the European Patent Office on Oct. 2, 2012 for Application No. 10762301.9 filed Apr. 6, 2010 (Applicant—Arizona Board of Regents / Inventors—Jian Li, et al.) (p. 1).

Extended Search Report issued by the European Patent Office on Sep. 13, 2012 for Application No. 10762301.9 filed Apr. 6, 2010 (Applicant—Arizona Board of Regents / Inventors—Jian Li, et al.) (pp. 1-7).

Amendments Received Before Examination filed with the European Patent Office on Mar. 9, 2012 for Application No. 10762301 filed Apr. 6, 2010 (Applicant—Arizona Board of Regents / Inventors—Jian Li, et al.)(pp. 1-8).

(Continued)

*Primary Examiner* — Charanjit Aulakh
(74) *Attorney, Agent, or Firm* — Fish & Richardson P.C.

(57) ABSTRACT

Platinum complexes that exhibit photoabsorption and photoemission, methods of making such complexes, and applications thereof are disclosed, including optical devices comprising the complexes.

6 Claims, 7 Drawing Sheets

(56) References Cited

FOREIGN PATENT DOCUMENTS

| | | | |
|---|---|---|---|
| JP | 2007-042875 A | 2/2007 | |
| JP | 2007-066581 A | 3/2007 | |
| JP | 2007-073620 A | 3/2007 | |
| JP | 2007-073845 A | 3/2007 | |
| JP | 2007-073900 A | 3/2007 | |
| JP | 2007-080593 A | 3/2007 | |
| JP | 2007-080677 A | 3/2007 | |
| JP | 2007-088105 A | 4/2007 | |
| JP | 2007-096259 A | 4/2007 | |
| JP | 2007-110067 A | 4/2007 | |
| JP | 2007-110102 A | 4/2007 | |
| JP | 2007-258550 A | 10/2007 | |
| JP | 2007-324309 A | 12/2007 | |
| JP | 2008-010353 A | 1/2008 | |
| JP | 2008-091860 A | 4/2008 | |
| JP | 2008-103535 A | 5/2008 | |
| JP | 2008-103535 A | 5/2008 | |
| JP | 2008-108617 A * | 5/2008 | ............. H01L 51/50 |
| JP | 2008-109085 A | 5/2008 | |
| JP | 2008-109103 A | 5/2008 | |
| JP | 2008-116343 A | 5/2008 | |
| JP | 2008-117545 A | 5/2008 | |
| JP | 2008-160087 A | 7/2008 | |
| JP | 2008-198801 A | 8/2008 | |
| JP | 2008-270729 A | 11/2008 | |
| JP | 2008-270736 A | 11/2008 | |
| JP | 2008-310220 A | 12/2008 | |
| JP | 2009-016184 A | 1/2009 | |
| JP | 2009-016579 A | 1/2009 | |
| JP | 2009-032977 A | 2/2009 | |
| JP | 2009-032988 A | 2/2009 | |
| JP | 2009267171 A | 11/2009 | |
| JP | 2009267244 A | 11/2009 | |
| JP | 2009283891 A | 12/2009 | |
| KR | 2007-061830 | 6/2007 | |
| KR | 2007112465 | 11/2007 | |
| WO | WO-00/70655 A2 | 11/2000 | |
| WO | WO-2004/108857 A1 | 12/2004 | |
| WO | WO-2006/033440 A1 | 3/2006 | |
| WO | WO-2006/098505 A1 | 9/2006 | |
| WO | WO-2006/115299 A1 | 11/2006 | |
| WO | WO-2006/115301 A1 | 11/2006 | |
| WO | WO-2008/066192 A1 | 6/2008 | |
| WO | WO-2008/066195 A1 | 6/2008 | |
| WO | WO-2008/066196 A1 | 6/2008 | |
| WO | WO-2008/117889 A1 | 10/2008 | |
| WO | WO-2008/123540 A2 | 10/2008 | |
| WO | WO-2009/017211 A1 | 2/2009 | |
| WO | WO-2010/118026 A2 | 10/2010 | |

OTHER PUBLICATIONS

Official Commumication issued by the European Patent Office on Dec. 7, 2011 for Application No. 10762301.9 filed Apr. 6, 2010 (Applicant—Arizona Board of Regents / Inventors—Jian Li, et al.) (pp. 1-2).

International Preliminary Report on Patentability issued by the International Searching Authority on Oct. 11, 2011 for PCT/US2010/030095 filed Apr. 6, 2010 and published as WO 2010/118026 on Oct. 14, 2010 (Applicant—Arizona Board of Regents / Inventors—Jian Li, et al.) (pp. 1-5).

International Search Report mailed by the International Searching Authority on Nov. 16, 2010 for PCT/US2010/030095 filed Apr. 6, 2010 and published as WO 2010/118026 on Oct. 14, 2010 (Applicant—Arizona Board of Regents / Inventors—Jian Li, et al.) (pp. 1-3).

Written Opinion issued by the International Searching Authority on Nov. 16, 2010 for PCT/US2010/030095 filed Apr. 6, 2010 and published as WO 2010/118026 on Oct. 14, 2010 (Applicant—Arizona Board of Regents / Inventors—Jian Li, et al.) (pp. 1-4).

Second Office Action issued by the Chinese Patent Office on Mar. 7, 2014 for Pat. App. No. 201080024040.X filed Apr. 6, 2010 and published as CN 102449108A on May 9, 2012 (Applicants—Arizona Technology Enterprises (AZTE); Inventors—Li et al.;) (6 pages).

English Translation of Second Office Action issued by the Chinese Patent Office on Mar. 7, 2014 for Pat. App. No. 201080024040.X filed Apr. 6, 2010 and published as CN 102449108A on May 9, 2012 (Applicants—Arizona Technology Enterprises (AZTE); Inventors—Li et al.;) (7 pages).

Response to Office Action (and English Translation) filed with the Chinese Patent Office on Jan. 13, 2014 for Pat. App. No. 201080024040.X filed Apr. 6, 2010 and published as Cn102449108A on May 9, 2012 (Applicants—Arizona Technology Enterprises (AZTE); Inventors—Li et al.;) (16 pages).

Official Action issued by the Japanese Patent Office on Mar. 13, 2014 for Pat. App. No. 2012-504779 filed Apr. 6, 2010 and published as JP 2012-522843 on Sep. 27, 2012 (Applicants—Arizona Technology Enterprises (AZTE); Inventors—Li et al.;) (5 pages).

Official Action (English translation only) issued by the Japanese Patent Office on Mar. 13, 2014 for Pat. App. No. 2012-504779 filed Apr. 6, 2010 and published as JP 2012-522843 on Sep. 27, 2012 (Applicants—Arizona Technology Enterprises (AZTE); Inventors—Li et al) (8 pages).

* cited by examiner

SYNTHESIS OF FOUR COORDINATED PLATINUM COMPLEXES AND THEIR APPLICATIONS IN LIGHT EMITTING DEVICES THEREOF

CROSS REFERENCE TO RELATED APPLICATIONS

The present application is a National Phase Application of International Application No. PCT/US2010/030095, filed Apr. 6, 2010, which claims priority to U.S. Provisional Patent Application No. 61/166,901, filed on Apr. 6, 2009, each of which is hereby incorporated by reference in its entirety.

BACKGROUND

1. Technical Field

The present disclosure relates to platinum complexes, and specifically to platinum complexes which are capable of absorbing and/or emitting light and are thus useful as emissive or absorption materials.

2. Technical Background

Compounds capable of absorbing and/or emitting light are ideally suited for use in a wide variety of optical and electro-optical devices, including photo-absorbing devices such as solar- and photo-sensitive devices, photo-emitting devices, such as organic light emitting diodes (OLEDs), or devices capable of both photo-absorption and emission. Much research has been devoted to the discovery and optimization of organic and organometallic materials for use in optical and electro-optical devices. Generally, research in this area aims to accomplish a number of goals, including improvements in absorption and emission efficiency, as well as improvements in processing ability, among others.

Despite significant advances in research devoted to optical and electro-optical materials, many current devices comprising organic or organometallic materials have yet to be optimized. Many materials currently used in optical and electro-optical devices have a number disadvantages, including poor processing ability, inefficient emission or absorption, and less than ideal stability, among others. Thus, a need exists for new materials which exhibit improved performance in optical and electro-optical devices. This need and other needs are satisfied by the present invention.

SUMMARY

The present invention relates to platinum complexes that exhibit photoabsorption and photoemission, to methods of making such compounds, and to applications thereof, including optical devices comprising the compounds.

In one aspect, the compounds are represented by the formula:

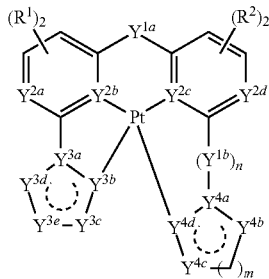

wherein each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol;

$R^3$ represents methyl, ethyl, propyl, or butyl;

$Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl;

n is an integer 0 or 1;

$Y^{1b}$, when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl;

each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol;

each of $Y^{3a}$, $Y^{3b}$, $Y^{3c}$, $Y^{3d}$, $Y^{3e}$, $Y^{4a}$, $Y^{4b}$, $Y^{4c}$, and $Y^{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl;

wherein m is an integer 1 or 2;

wherein the open dotted circle

indicates partial or full unsaturation of the ring with which it is associated;

provided that if m is 1, each of $Y^{2a}$ and $Y^{2d}$ is CH and each of $Y^{2b}$ and $Y^{2c}$ is N, then at least one of $Y^{4a}$, $Y^{4b}$, $Y^{3a}$, or $Y^{3d}$ is not N; and provided that if n is 0, m is 2, each of $Y^{2a}$ and $Y^{2d}$ is CH, and each of $Y^{2b}$ and $Y^{2c}$ is N, then at least one of $Y^{3b}$ or $Y^{3c}$ is not N.

Also disclosed are optical devices, such as organic light emitting devices, photovoltaic devices (e.g., solar cells), and luminescent display devices that comprise one or more compounds of the invention as a functional material, such as a light-emitter or absorber, or both.

BRIEF DESCRIPTION OF THE FIGURES

The accompanying figures, which are incorporated in and constitute a part of this specification, illustrate several aspects and together with the description serve to explain the principles of the invention.

Figure 1:
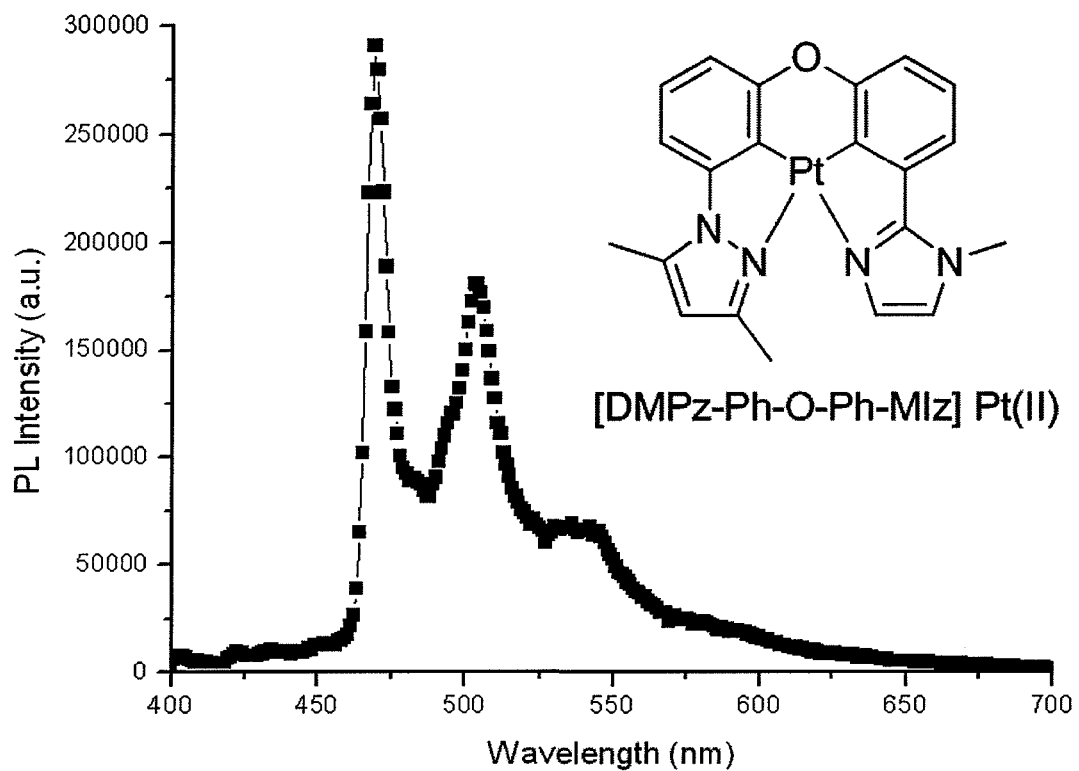
FIG. 1 is a photoluminescence spectrum produced from a specific aspect, [DMPz-Ph-O-Ph-MIz]Pt (II) taken in dichloromethane at 77 K.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The terms "amine" or "amino" as used herein are represented by the formula NA$^1$A$^2$A$^3$, where A$^1$, A$^2$, and A$^3$ can be, independently, hydrogen or optionally substituted alkyl, cycloalkyl, alkenyl, cycloalkenyl, alkynyl, cycloalkynyl, aryl, or heteroaryl group as described herein.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "nitrile" as used herein is represented by the formula —CN.

The term "thiol" as used herein is represented by the formula —SH.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

In one aspect, the compounds of the present invention can be represented by the formula:

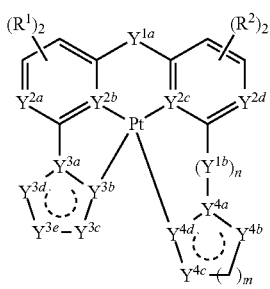

In such an aspect, each $R^1$ and $R^2$ in $(R^1)_2$ and $(R^2)_2$ independently represents hydrogen, optionally substituted $C_1$-$C_4$ alkyl, halogen, hydroxyl, amino, nitro, or thiol; $R^3$ represents methyl, ethyl, propyl, or butyl; $Y^{1a}$ represents O, S, $NR^{4a}$, wherein $R^{4a}$ represents optionally substituted $C_1$-$C_4$ alkyl; $Si(R^{4b})_2$, wherein each $R^{4b}$ in $(R^{4b})_2$ independently represents optionally substituted $C_1$-$C_4$ alkyl; or $C(R^{4c})_2$, wherein each $R^{4c}$ in $(R^{4c})_2$ represents hydrogen or optionally substituted $C_1$-$C_4$ alkyl; n is an integer 0 or 1; $Y^{1b}$, when present, represents O, S, $NR^{5a}$, wherein $R^{5a}$ represents optionally substituted $C_1$-$C_4$ alkyl; $Si(R^{5b})_2$, wherein each $R^{5b}$ in $(R^{5b})_2$ independently represents optionally substituted $C_1$-$C_4$ alkyl; or $C(R^{5c})_2$, wherein each $R^{5c}$ in $(R^{5c})_2$ represents hydrogen or optionally substituted $C_1$-$C_4$ alkyl; each of $Y^{2a}$, $Y^{2b}$, $Y^{2c}$, and $Y^{2d}$ independently represents N, $NR^{6a}$, or $CR^{6b}$, wherein each of $R^{6a}$ and $R^{6b}$ independently represents hydrogen, optionally substituted $C_1$-$C_4$ alkyl, halogen, hydroxyl, amino, nitro, or thiol; each of $Y^{3a}$, $Y^{3b}$, $Y^{3c}$, $Y^{3d}$, $Y^{3e}$, $Y^{4a}$, $Y^{4b}$, $Y^{4c}$, and and $Y^{4d}$ independently represents N, O, S, $NR^{6a}$, $CR^{6b}$, wherein each of $R^{6a}$ and $R^{6b}$ independently represents hydrogen or optionally substituted $C_1$-$C_4$ alkyl; or $Z(R^{6c})_2$, wherein Z is C or Si, and wherein each $R^{6c}$ in $(R^{6c})_2$ independently represents hydrogen or optionally substituted $C_1$-$C_4$ alkyl; m is an integer 1 or 2; wherein the open dotted circle

indicates partial or full unsaturation of the ring with which it is associated.

In one aspect of the formula above, if m is 1, each of $Y^{2a}$ and $Y^{2d}$ is CH and each of $Y^{2b}$ and $Y^{2c}$ is N, then at least one of $Y^{4a}$, $Y^{4b}$, $Y^{3a}$, or $Y^{3d}$ is not N. For example, according to this aspect, the following compound is not included in the above formula:

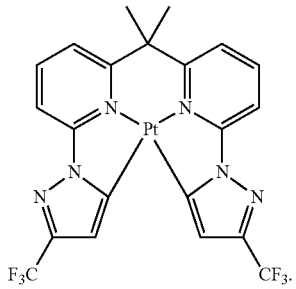

As can be seen in the preceding example above, m is 1, each of $Y^{2a}$ and $Y^{2d}$ is CH and each of $Y^{2b}$ and $Y^{2c}$ is N. However, each of $Y^{4a}$, $Y^{4b}$, $Y^{3a}$, or $Y^{3d}$ is N. It follows that the preceding example, according to this aspect, is not included within the general formula above. In the practice of this aspect, similar analysis can be used to determine whether or not a compound is or is not included within the general formula above.

In a further aspect of the general formula above, if n is 0, m is 2, each of $Y^{2a}$ and $Y^{2d}$ is CH, and each of $Y^{2b}$ and $Y^{2c}$ is N, then at least one of $Y^{3b}$ or $Y^{3c}$ is not N. For example, according to this aspect, the following compound is not included in the above formula:

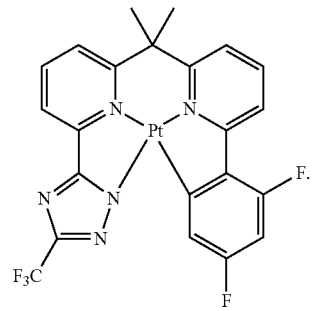

As can be seen in the preceding example above, n is 0, m is 2, each of $Y^{2a}$ and $Y^{2d}$ is CH, and each of $Y^{2b}$ and $Y^{2c}$ is N. However, each of $Y^{3b}$ and $Y^{3c}$ is N. It follows that the preceding example, according to this aspect, is not included within the general formula above. Once more, in the practice of this aspect, similar analysis can be used to determine whether or not a compound is or is not included within the general formula above.

In one aspect of the general formula above, the compound is represented by the formula:

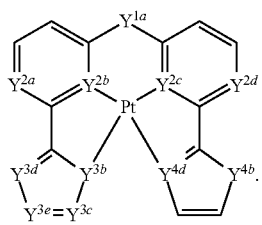

In other non-limiting aspects, examples of specific aspects within this formula can include one or more of the following:

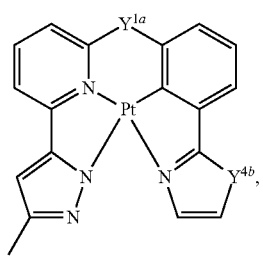

-continued

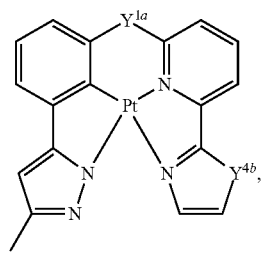

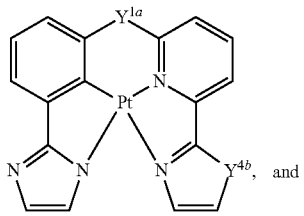

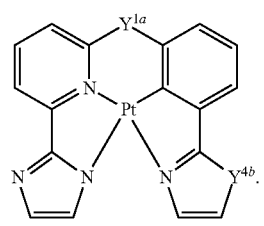

In other non-limiting aspects, examples of specific aspects within this formula can include one or more of the following:

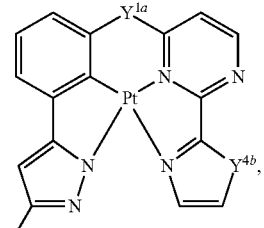

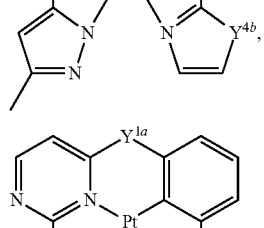

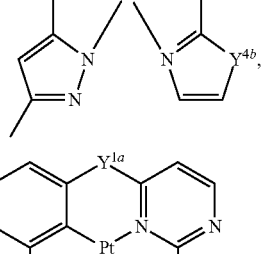

-continued

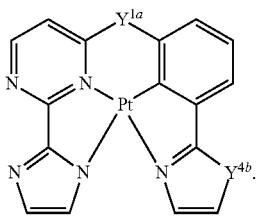

In another aspect of the general formula above, the compound is represented by the formula:

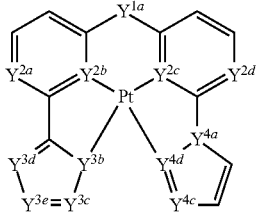

In other aspects, non-limiting examples of specific aspects within this formula can include one or more of the following:

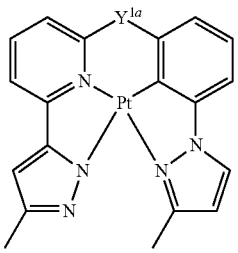

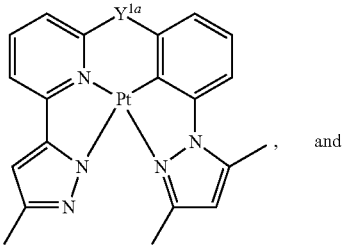

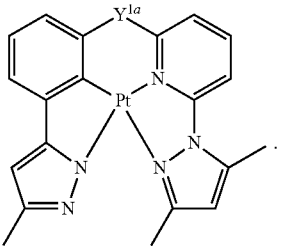

In other aspects, non-limiting examples of specific aspects within this formula can include one or more of the following:

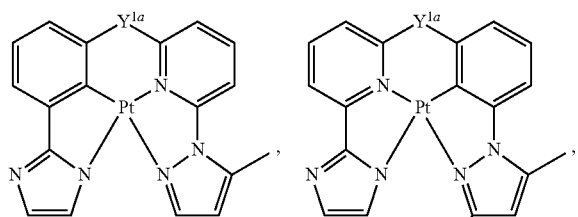

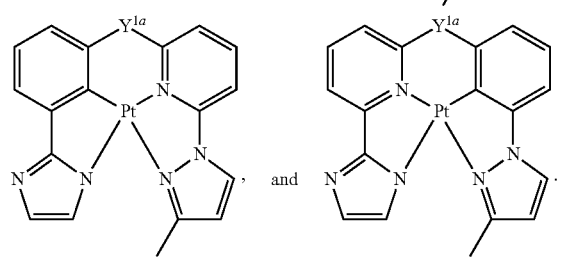, and 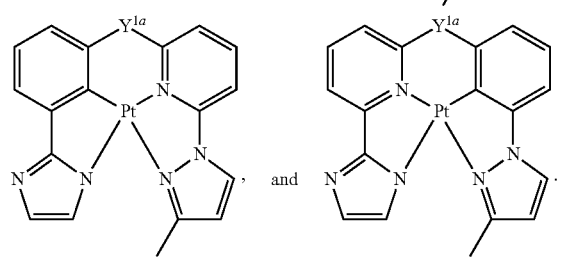.

In other aspects, non-limiting examples of specific aspects within this formula can include one or more of the following:

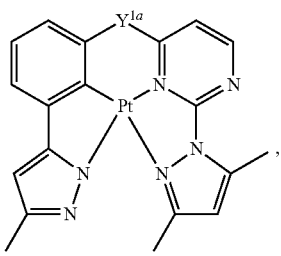

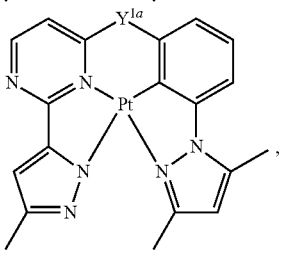

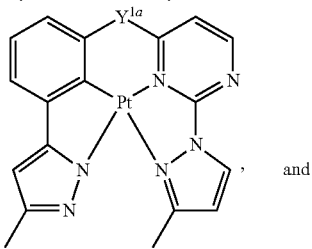, and

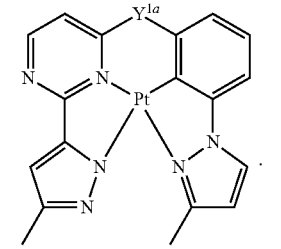.

In other aspects, non-limiting examples of specific aspects within this formula can include one or more of the following:

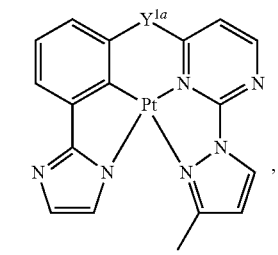

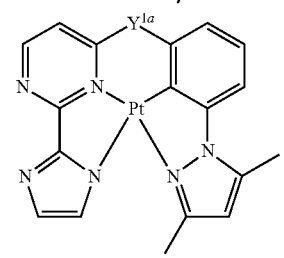

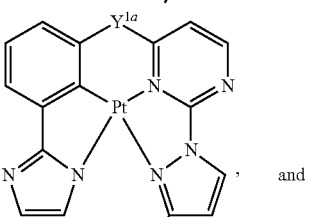, and

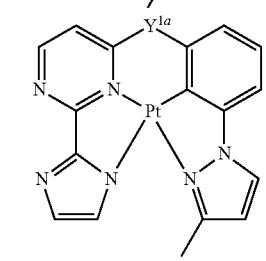.

In other aspects, non-limiting examples of specific aspects within this formula can include one or more of the following:

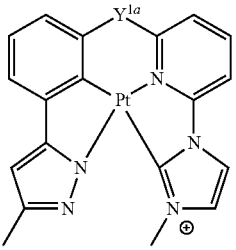 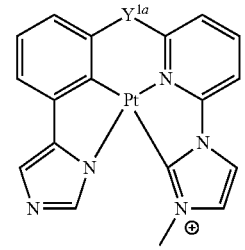

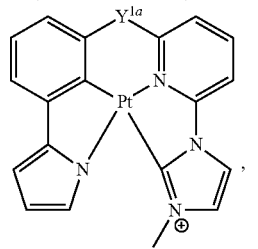, and 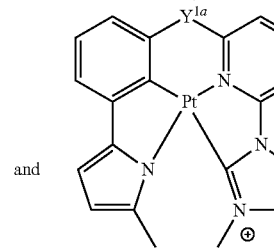.

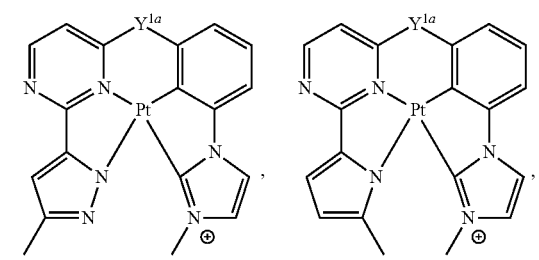

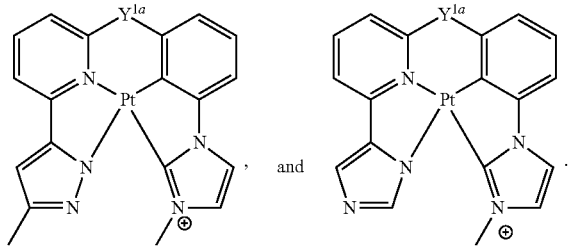

In other aspects, non-limiting examples of specific aspects within this formula can include one or more of the following:

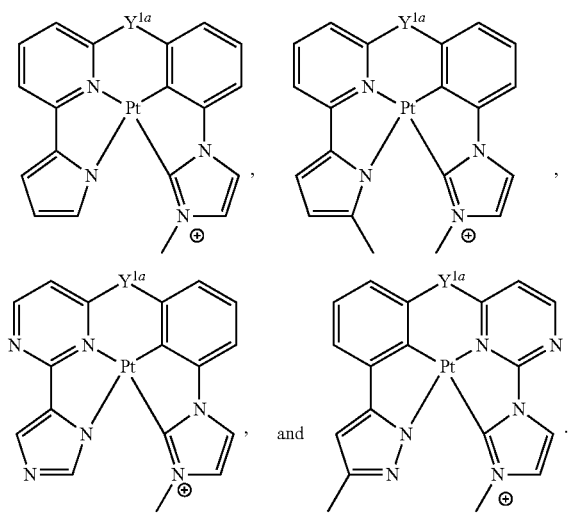

In other aspects, non-limiting examples of specific aspects within this formula can include one or more of the following:

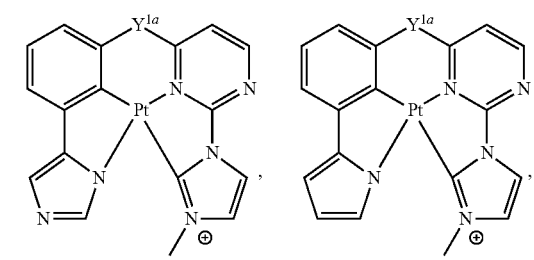

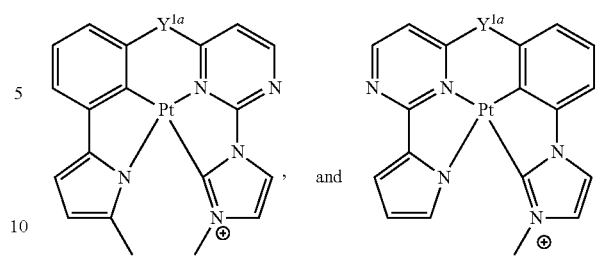

In another aspect of the general formula above, the compound is represented by the formula:

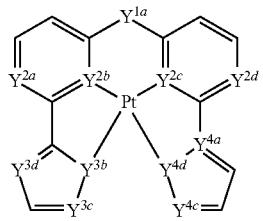

In other aspects, non-limiting examples of specific aspects within this formula can include one or more of the following:

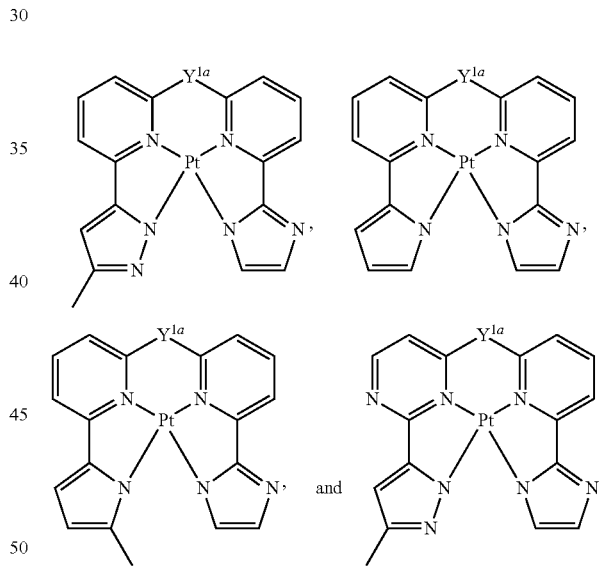

In other aspects, non-limiting examples of specific aspects within this formula can include one or more of the following:

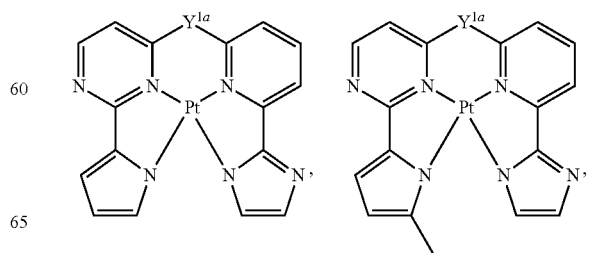

-continued

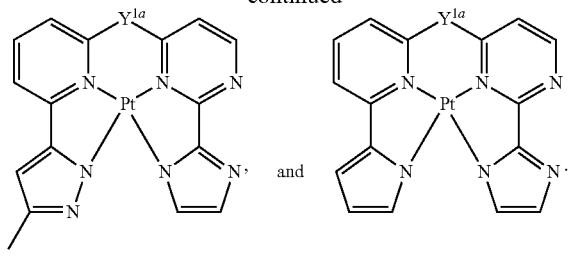

In other aspects, non-limiting examples of specific aspects within this formula can include one or more of the following:

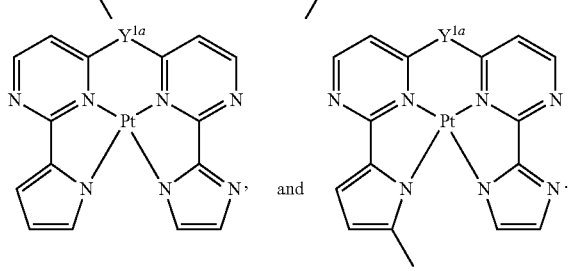

In another aspect of the general formula above, the compound is represented by the formula:

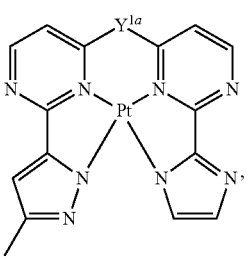

In other aspects, non-limiting examples of specific aspects within this formula can include one or more of the following:

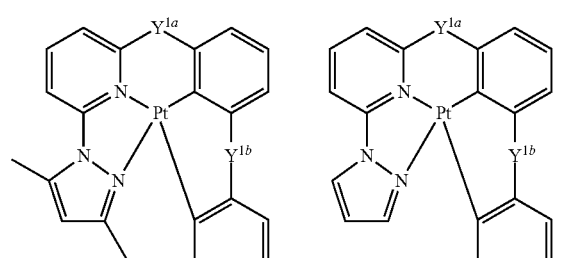

-continued

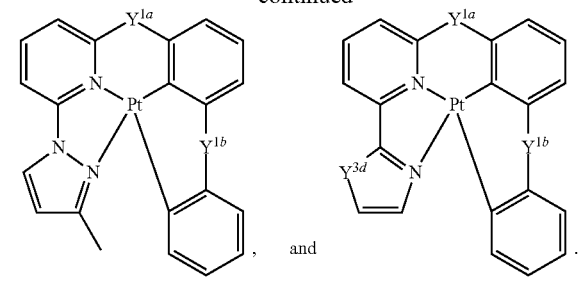

In other aspects, non-limiting examples of specific aspects within this formula can include one or more of the following:

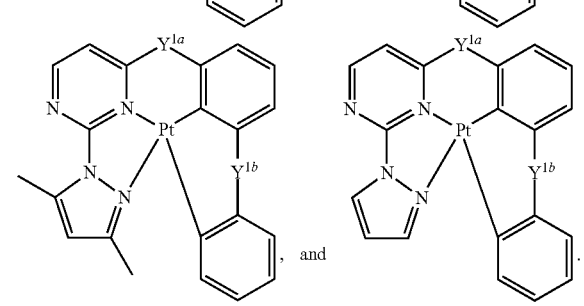

In other aspects, non-limiting examples of specific aspects within this formula can include one or more of the following:

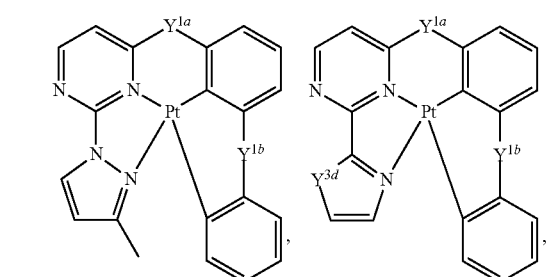

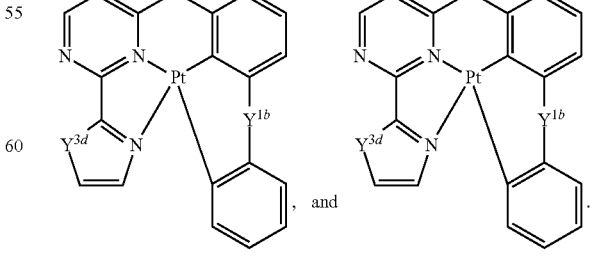

In other aspects, non-limiting examples of specific aspects within this formula can include one or more of the following:

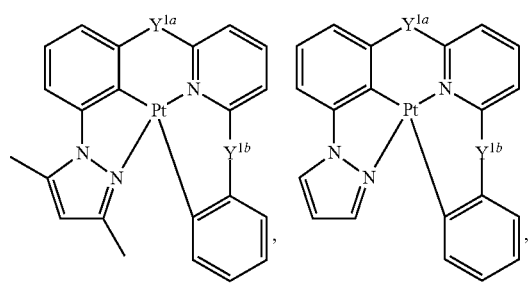

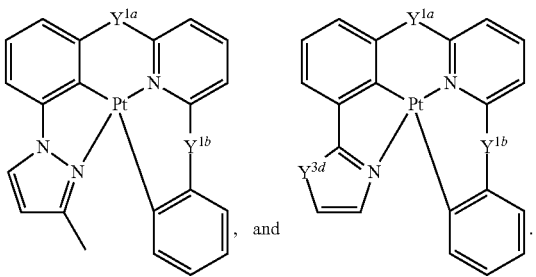

In other aspects, non-limiting examples of specific aspects within this formula can include one or more of the following:

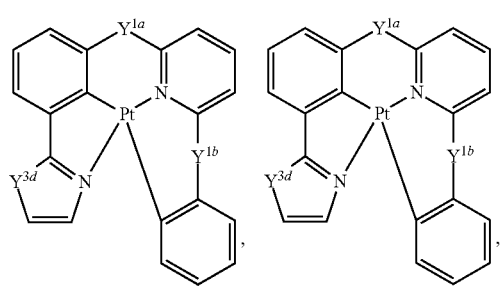

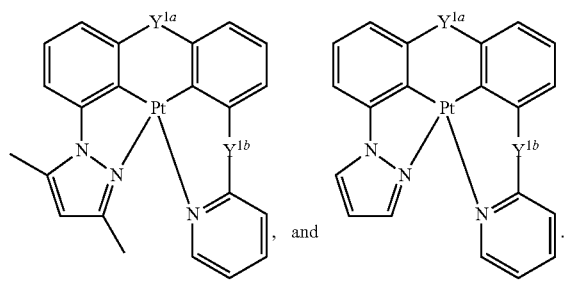

In other aspects, non-limiting examples of specific aspects within this formula can include one or more of the following:

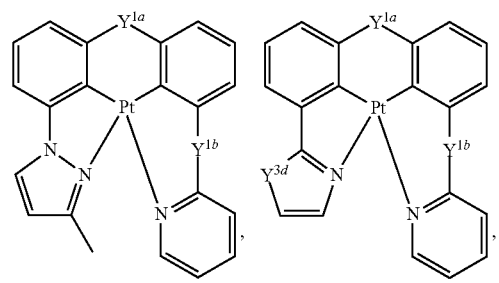

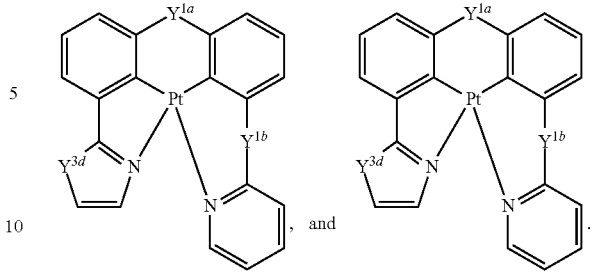

In other aspects, non-limiting examples of specific aspects within this formula can include one or more of the following:

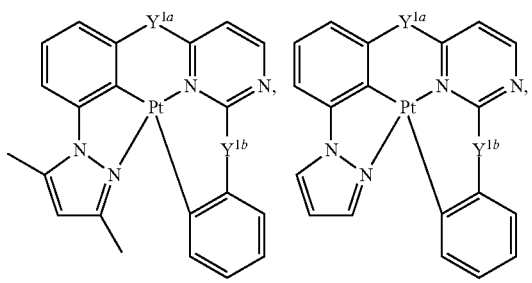

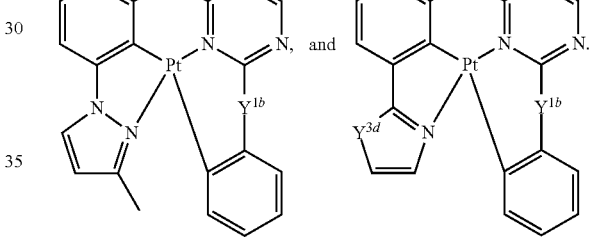

In other aspects, non-limiting examples of specific aspects within this formula can include one or more of the following:

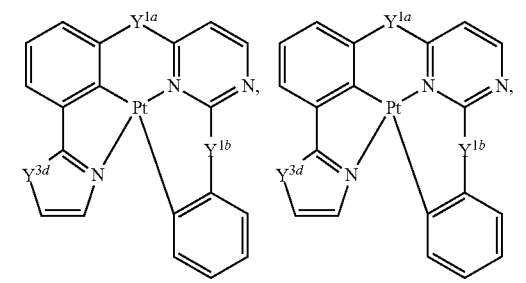

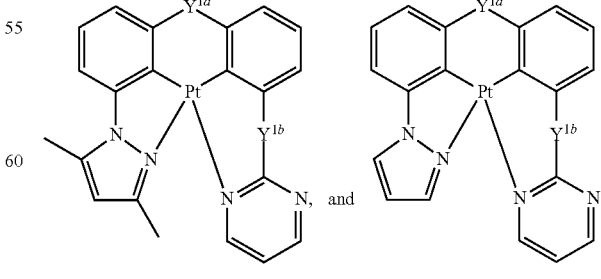

In other aspects, non-limiting examples of specific aspects within this formula can include one or more of the following:

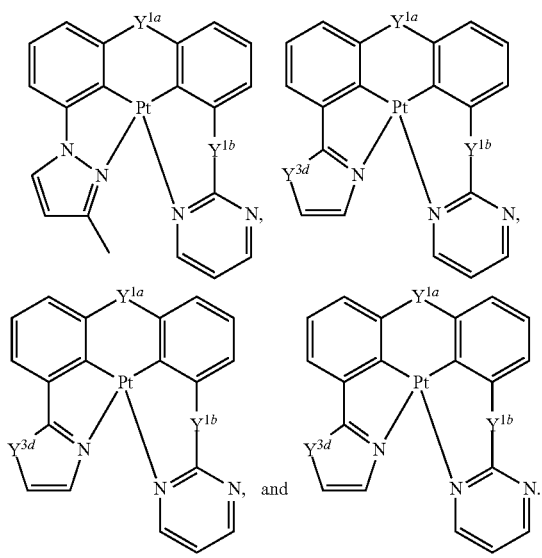

In other aspects, non-limiting examples of specific aspects within this formula can include one or more of the following:

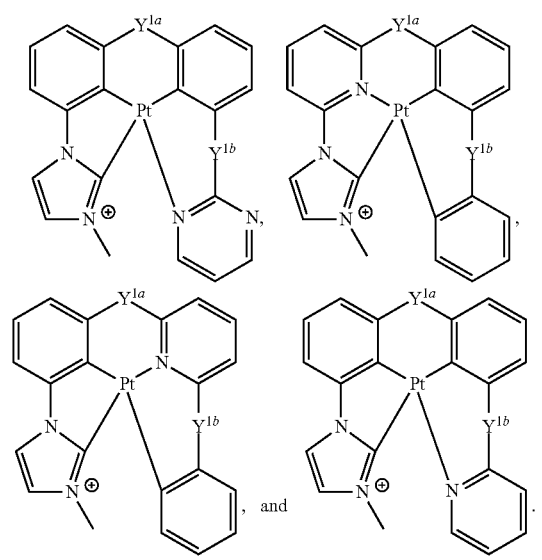

In other aspects, non-limiting examples of specific aspects within this formula can include one or more of the following:

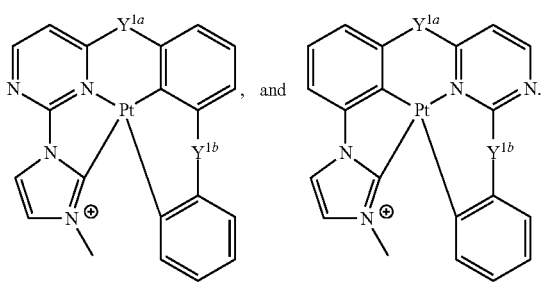

In another aspect of the general formula above, the compound is represented by the formula:

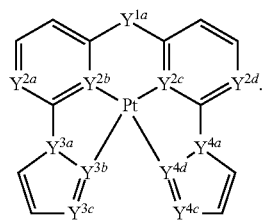

Non-limiting examples of specific aspects within this formula include:

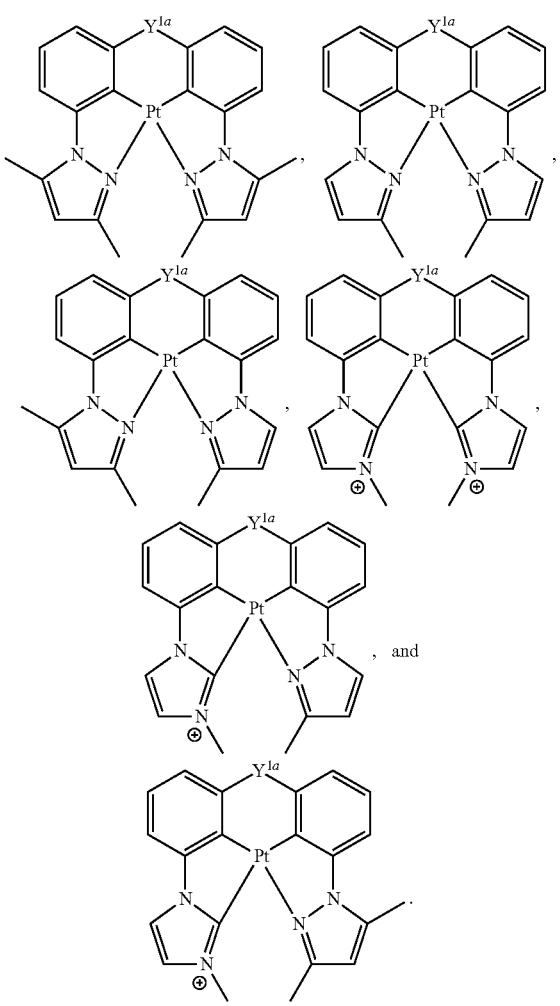

In another aspect of the general formula above, the compound is represented by the formula:

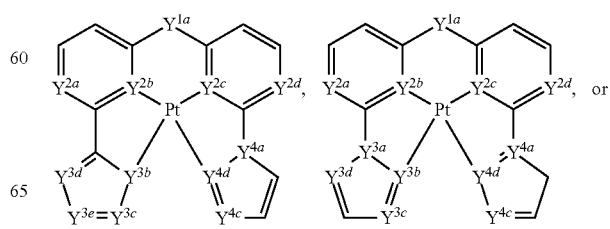

-continued

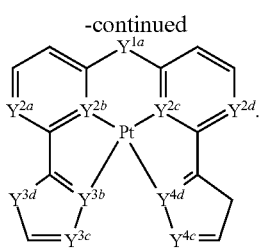

In other aspects, non-limiting examples of specific aspects within these formula can include one or more of the following:

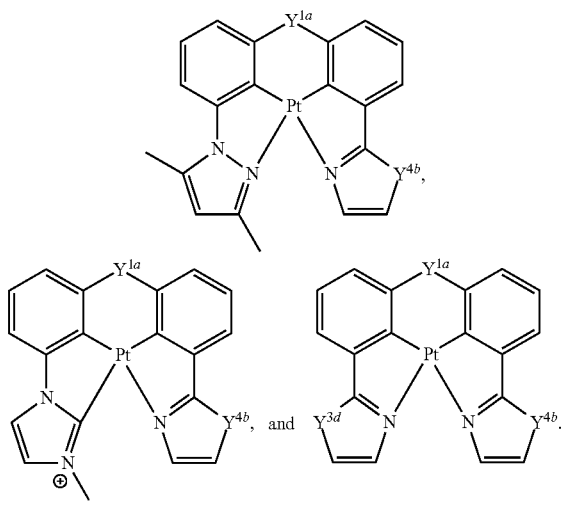

In one aspect, the inventive compound can comprise:

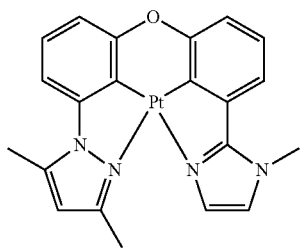

[DMPz—Ph—O—Ph—MIz] Pt(II).

In another aspect, the inventive compound can comprise:

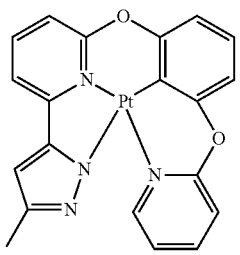

[MPz—Py—O—Ph—O—Py] Pt(II).

In another aspect, the inventive compound can comprise:

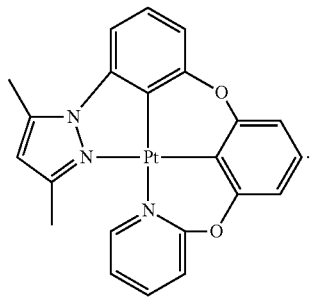

In another aspect, the inventive compound can comprise:

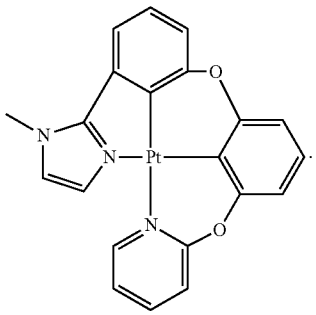

In another aspect, the inventive compound can comprise:

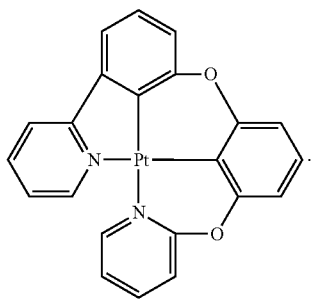

In another aspect, the inventive compound can comprise:

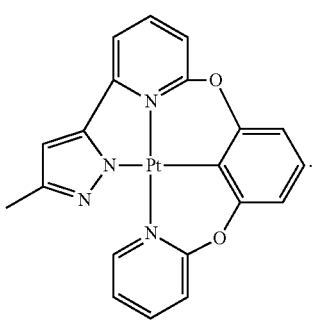

The compounds of the invention can be made using a variety of methods. In one aspect, wherein $Y^{1a}$ is O, the compounds can be provided according to Scheme 1.

Scheme 1.

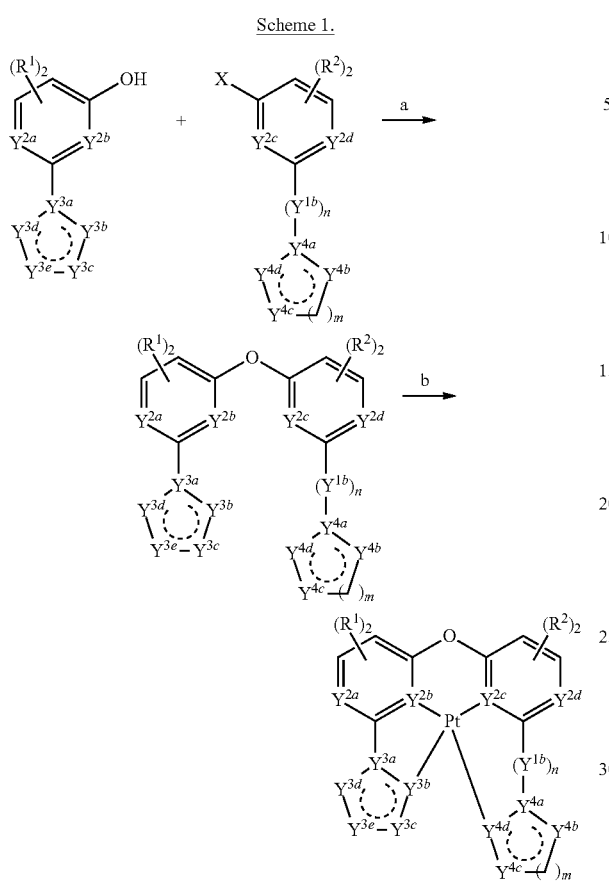

With reference to Scheme 1, step "a" can be accomplished, for example, by using a catalytic amount of a coupling reagent, such as $Cu_2O$, which couples alcohols, particularly phenols, with halogenated phenyl groups. In one aspect, the variable "X" in Scheme 1 above represents halogen (i.e., Cl, F, I, Br), and can be I when used in conjunction with Scheme 1.

Each side of the ligand which complexes the metal can be made independently using a variety of methods, which generally depend on whether $Y^{3a}$ is N or C. In another aspect with reference to Scheme 2 below, when $Y^{4a}$ is N, the precursor can be provided according to Scheme 2(A), wherein a halogenated phenyl compound is reacted with a pyrazole, imadazole, 1H-1,2,3-triazole, 1H-tetrazole, or 2H-pentazole. In one aspect, the halogenated phenyl compound can comprise any halogen (X), including Cl, Br, F, or I, but is preferably I, which is typically more reactive in a coupling reaction. The halogenated phenyl compound and corresponding pyrazole, imadazole, 1H-1,2,3-triazole, 1H-tetrazole, or 2H-pentazole can be coupled using a metallic or organometallic coupling agent, such as $Cu_2O$. During such a coupling reaction, it can be advantageous to include an acid scavenger, such as syn-2-pyridinealdoxime, in a small molar ratio, for example 20 mol %.

Alternatively, when $Y^{4a}$ is C, a different protocol can be used to provide the precursor. In another aspect with reference to Scheme 2(B) below, a halogenated phenyl, as discussed above is reacted with a tetrazole, 1,2,3-triazole, pyrazole, or pyrrole to achieve a carbon-carbon bond coupling, as opposed to a carbon-nitrogen bond coupling as shown in Scheme 2(A). The carbon-carbon bond coupling can also be achieved using an organometallic catalyst, such as a Pd(II) catalyst (e.g., $Pd(OAc)_2$) in a small molar ratio, which is typically used together with an excess of a salt mixture, such as KI and CuI. As one of skill in the art understands, when employing each of the coupling reactions shown in Scheme 2, it can be advantageous to perform the reactions in a dry atmosphere, for example under argon, or even in a dry box to avoid moisture or oxygen inclusion.

Scheme 2.

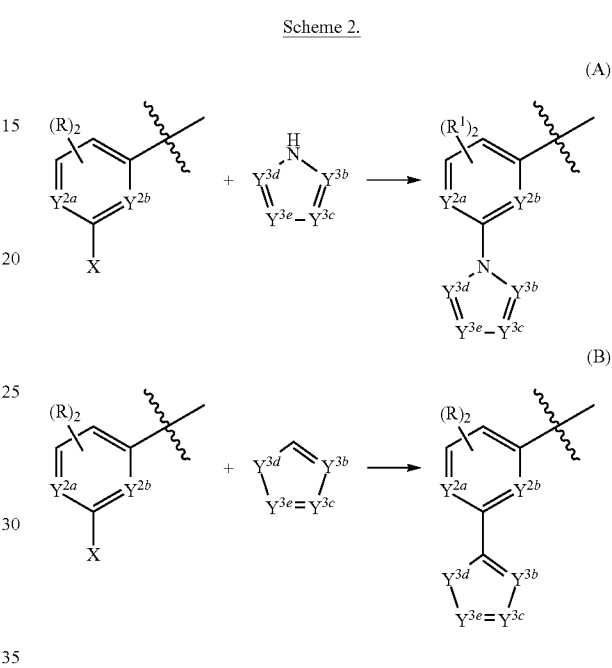

In one aspect, the compounds, reagents, such as, for example, coupling agents, and/or catalysts described herein with respect to the preparation of one or more of the inventive compounds are commercially available. One of skill in the art, in possession of the teachings of this disclosure, could readily select an appropriate compound, reagent, and/or catalyst to prepare a specific inventive compound.

In another aspect, the compounds of the invention can be useful in a variety of optical applications. In one aspect, any one or more of the inventive compounds can be used as an emitter, an absorber, or a combination thereof in an electronic device, such as, for example, a light emitting device. It should be noted that an inventive compound can be used as-is or can be formed into a composite and/or layer to be used in such a device. In one aspect, a layer is formed from one or more inventive compounds, the layer to be positioned in the device. In another aspect, a composite material can be formed using one or more of the inventive compounds, the composite material to be positioned in the device. It should be noted that multiple compounds of the same or varying composition can be utilized within the same layer or composite. In other aspects, a layer or composite can also optionally comprise one or more additional components, such as, for example, a host material, a polymer, a processing aid, a charge transport material, or a combination thereof. In another aspect, multiple layers can be assembled, for example, in overlying registration or substantially overlying registration, to provide desired emissive and/or absorptive properties. For example, multiple layers of differing compounds can be provide to provide a desired emission spectrum. In one aspect, any one or more individual layers in a device, or any portion thereof, can be individually addressable.

In another aspect, the compounds can be useful in organic light emitting diodes (OLED)s, luminescent devices and displays, and other light emitting devices as light emitting materials. With reference to FIG. 1, for example, a specific aspect, [DMPz-Ph-O-Ph-MIz]Pt(II) exhibits photoluminescence (absorption of light followed by emission of light) across a range of wavelengths, including a narrow blue emission and other emission bands in the red to near-IR regions of the spectrum.

The emission (and absorption) profile of the compounds can be tuned by varying the structure of the ligand surrounding the metal center. For example, and while not wishing to be bound by theory, compounds having a ligand with electron withdrawing substituents will generally exhibit different optical properties, including emission and absorption, than compounds having a ligand with electron donating substituents. In one aspect, a chemical structural change can affect the electronic structure of the compound, thereby affecting the absorption and emission of the compound. Thus, in various aspects, the compounds of the present invention can be tailored or tuned to a specific application that desires a particular emission or absorption characteristic.

Figure 2:
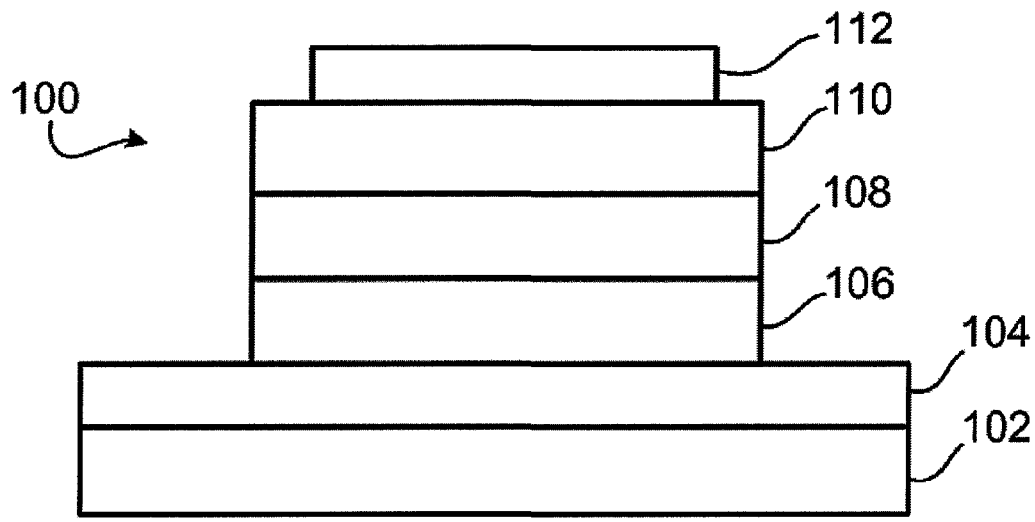
FIG. 2 is a drawing of a cross-section of an exemplary organic light-emitting diode (OLED).
Figure 3:
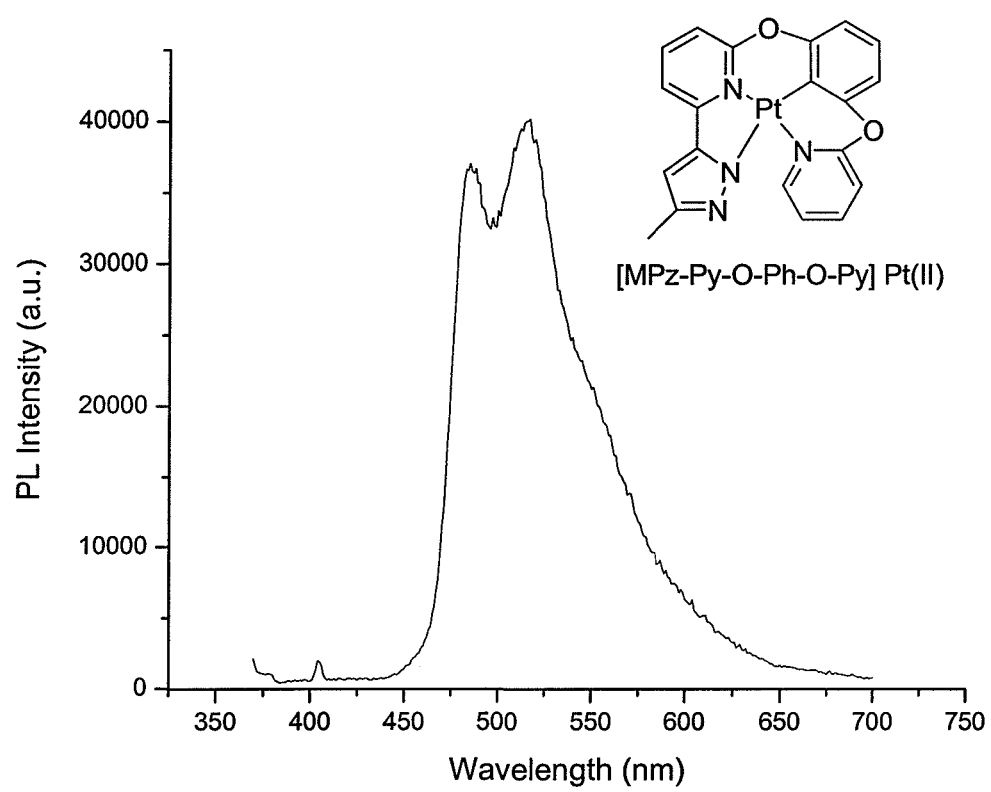
FIG. 3 is a photoluminescence spectrum produced from a specific aspect, [MPz-Py-O-Ph-O-Py]Pt (II) taken in dichloromethane at room temperature.

In one aspect, one or more of the inventive compounds can be used in an OLED. FIG. 2 shows a cross-sectional view of an OLED 100, which includes substrate 102 with an anode 104, which is typically a transparent material, such as indium tin oxide (ITO), a layer of hole-transporting material(s) (HTL) 106, a layer of light processing material 108, such as an emissive material (EML) including an emitter and a host, a layer of electron-transporting material(s) (ETL) 110, and a metal cathode layer 112.

In this aspect, the layer of light processing material 108 can comprise one or more compounds of the present invention optionally together with a host material. The host material can be any suitable host material known in the art. The emission color of an OLED is determined by the emission energy (optical energy gap) of the light processing material 108, which as discussed above can be tuned by tuning the electronic structure of the emitting compounds and/or the host material. Both the hole-transporting material in the HTL layer 106 and the electron-transporting material(s) in the ETL layer 110 can comprise any suitable hole-transporter known in the art. Components and designs for the fabrication of light emitting and/or absorbing devices are commercially available and one of skill in the art could readily select, in possession of the teachings of this disclosure, suitable components and designs to fabricate a device.

It will be apparent that the compounds of the present invention can exhibit phosphorescence. Phosphorescent OLEDs (i.e., OLEDs with phosphorescent emitters) typically have higher device efficiencies that other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

In one aspect, light emitted from an OLED device is typically produced via a fluorescence and/or a phosphorescence process. In various aspects, OLEDs can be comprised of at least two thin organic layers separating the anode and cathode of the device. In one aspect, the material of at least one of these layers can be selected based on the material's ability to transport holes, and the material of at least one other layer can be selected based on its ability to transport electrons.

In another aspect, it can be desirable for OLEDs to be fabricated using materials that provide electroluminescent emission in a relatively narrow band centered near selected spectral regions, corresponding to one or more of the three primary colors so that they may be used as a colored layer in an OLED. In another aspect, it can be desirable that such compounds be capable of being readily deposited as a thin layer using vacuum deposition techniques so that they may be readily incorporated into an OLED that is prepared entirely from vacuum-deposited organic materials. In one aspect, any one or more of the inventive compounds described herein can be formed into a thin layer. In another aspect, any one or more of the inventive compounds described herein can be formed into a thin layer by, for example, a vacuum deposition technique, a thermal deposition technique, a spin-coating technique, or a combination thereof. In other aspects, other coating and/or film forming technologies known in the art can be utilized, provided that such techniques do not destroy and/or adversely affect the light emitting and/or light absorbing properties of the inventive compound.

In one aspect, a general schematic of an exemplary OLED device was described above. In another aspect, the arrangement of layers in an OLED device can comprise a hole transport layer and an electron transporting layer, with an emissive layer therebetween, wherein each of the layers is in at least partially overlying registration. In another aspect, other layers can optionally be present adjacent to or between any other recited layers. In one exemplary aspect, an exciton blocking layer positioned between the emissive layer and the electron transporting layer.

In one aspect, an emissive layer can be formed with a host material in which the emissive molecule are present as a guest or the emissive layer may be formed of the emissive molecule itself. In the former case, the host material may be a hole-transporting matrix, such as, for example, a substituted triaryl amine. In another aspect, a host material can comprise 4,4'-N,N'-dicarbazole-biphenyl (CBP).

In yet another aspect, an emissive layer can also contain a polarization molecule that can affects the wavelength of light emitted when a dopant luminesces.

In yet another aspect, a layer formed of an electron transporting material can be used to transport electrons into an emissive layer comprising an emissive molecule and optional host material. In various aspects, an electron transport material can comprise an electron-transporting matrix, such as, for example, metal quinoxolates, oxidazoles and triazoles. In one aspect, an exemplary electron transport material is tris-(8-hydroxyquinoline)aluminum (Alq3).

In another aspect, an exemplary hole transporting material is 4,4'-bis[N-(1-naphthyl)-N-phenyl-amino]biphenyl (NPD).

In one aspect, the use of an exciton blocking layer to confine excitons within a luminescent layer can be advantageous. In one aspect, the blocking layer may be placed between a luminescent layer and an electron transport layer for a hole-transporting host. In one aspect, an exemplary material for such a barrier layer is bathocuproine (BCP).

In one aspect, a layer of one or more inventive compounds can be deposited by thermal evaporation onto substrate, such as, for example, a clean glass substrate, precoated with indium tin oxide. A 400 Å thick layer of 4,4'-bis(N-(1-naphthyl)-N-phenyl-amino]biphenyl can then be used to transport holes to a luminescent layer consisting of Ir(ppy)$_3$ in CBP.

In another aspect, other techniques known to one of ordinary skill can be used in conjunction with the compositions and methods of the present invention. For example, in one aspect, a LiF cathode can be used. In another aspect, a shaped substrate can be used. In yet another aspect, a hole transport material can be used that can result in a reduction in operating voltage or increased quantum efficiency of the resulting device.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

In one aspect, an electronic device, such as, for example, an organic light emitting diode, comprises the following compound as an emitter, an absorber, or a combination thereof:

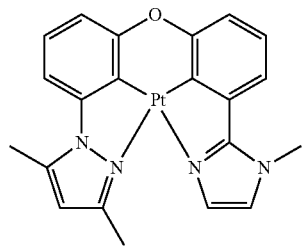

[DMPz—Ph—O—Ph—MIz] Pt(II).

In one aspect, an electronic device, such as, for example, an organic light emitting diode, comprises the following compound as an emitter, an absorber, or a combination thereof:

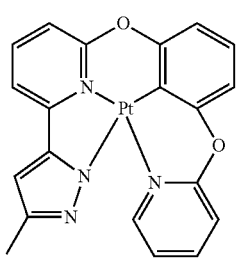

[MPz—Py—O—Ph—O—Py] Pt(II).

In one aspect, an electronic device, such as, for example, an organic light emitting diode, comprises the following compound as an emitter, an absorber, or a combination thereof:

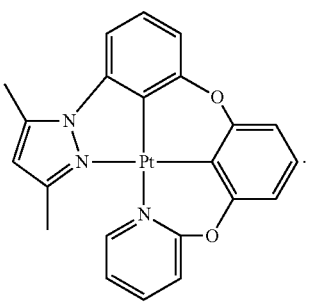

In one aspect, an electronic device, such as, for example, an organic light emitting diode, comprises the following compound as an emitter, an absorber, or a combination thereof:

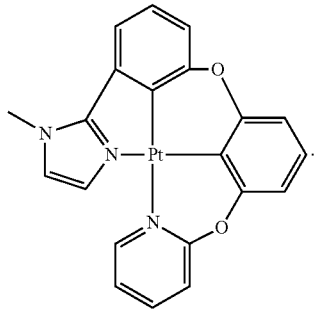

In one aspect, an electronic device, such as, for example, an organic light emitting diode, comprises the following compound as an emitter, an absorber, or a combination thereof:

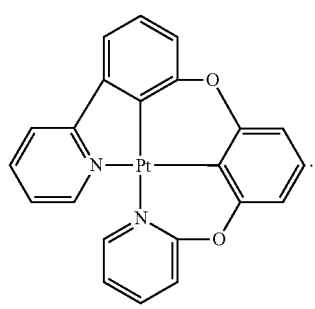

In one aspect, an electronic device, such as, for example, an organic light emitting diode, comprises the following compound as an emitter, an absorber, or a combination thereof:

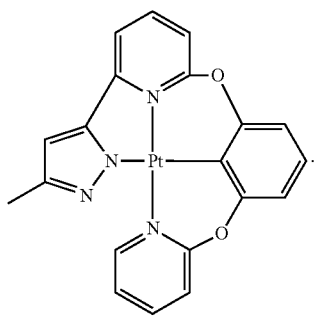

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Preparation of Specific Aspect [(DMPz-Ph)$_2$-O]Pt(II)

Synthesis of DMPz-Ph-OH

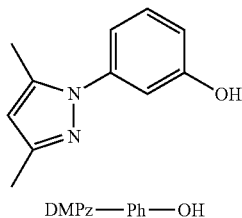

DMPz—Ph—OH

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), 3,5-dimethylpyrazole (1.1 mmol), Cs$_2$CO$_3$ (2.5 mmol), 3-iodophenol (1.0 mmol), and anhydrous and degassed dimethylformamide (DMF) (40 mL). The flask was stirred and heated under microwave irradiation for 2 hours. The reaction mixture was allowed to cool to room temperature, diluted with dichloromethane and filtered through a plug of CELITE™, the filter cake being further washed with dichloromethane (20 mL). The filtrate was concentrated under vacuo to yield a residue, which was purified by column chromatography on silica gel to obtain the pure product DMPz-Ph-OH in 50% yield. $^1$H NMR (CDCl$_3$, 500 MHz): δ2.26 (s, 1H), 2.26 (s, 3H), 2.30 (s, 3H), 5.98 (s, 1H), 6.73-6.78 (m, 2H), 7.11 (dd, 1H), 7.18 (dd, 1H).

Synthesis of DMPz-Ph-I

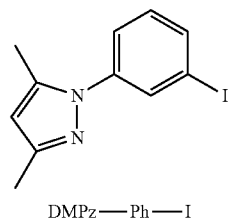

DMPz—Ph—I

After standard cycles of evacuation and back-fill with dry and pure nitrogen, an oven-dried Schienk flask equipped with a magnetic stir bar was charged with Cu$_2$O (0.1 mmol, 10 mol %), syn-2-pyridinealdoxime (0.4 mmol, 20 mol %), 3,5-dimethylpyrazole (1.1 mmol), Cs$_2$CO$_3$ (2.5 mmol), 1,3-diiodobenzene (1.0 mmol), and anhydrous and degassed acetonitrile (40 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product DMPz-Ph-I in 40% yield. $^1$H NMR (CDCl$_3$, 500 MHz): δ2.30 (s, 3H), 2.32 (s, 3H), 6.00 (s, 1H), 7.22 (dd, 1H), 7.40 (d, 1H), 7.67 (d, 1H), 7.84 (s, 1H).

Synthesis of (DMPz-Ph)$_2$-O

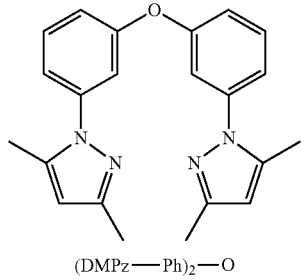

(DMPz—Ph)$_2$—O

After standard cycles of evacuation and back-fill with dry and pure nitrogen, an oven-dried Schlenk flask equipped with a magnetic stir bar was charged with Cu$_2$O (0.1 mmol, 10 mol %), DMPz-Ph-OH (1.0 mmol), K$_2$CO$_3$ (2.5 mmol), DMPz-Ph-I (1.0 mmol), and anhydrous and degassed DMAc (20 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product (DMPz-Ph)$_2$-O in 70% yield. $^1$H NMR (d$_6$-DMSO$_3$, 400 MHz): δ2.66 (s, 6H), 3.29 (s, 6H), 6.29 (s, 2H), 7.14 (dd, 2H), 7.43 (dd, 2H), 7.51 (dd, 2H), 8.16 (dd, 2H).

Synthesis of [(DMPz-Ph)$_2$-O]Pt(II)

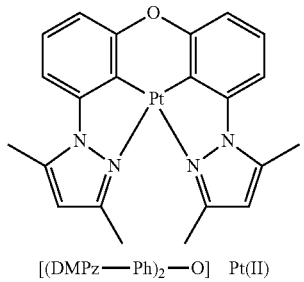

[(DMPz—Ph)$_2$—O] Pt(II)

A mixture of (DMPz-Ph)$_2$-O (1 mmol), K$_2$PtCl$_4$ (0.41 mg, 1 mmol), and acetic acid (10 mL) was refluxed for 3 days. The mixture was allowed to cool to room temperature. The resulting yellow complex was filtered off and washed with MeOH, H$_2$O, EtOH, and Et$_2$O, and dried under vacuum to produce [(DMPz-Ph)$_2$-O]Pt(II) in 90% yield. The product was purified by recrystallization from dimethyl sulfoxide/methanol for further testing.

Example 2

Preparation of Specific Aspect [DMPz-Ph-O-Ph-MIz]Pt (II)

Synthesis of MIz-Ph-OH

MIz—Ph—OH

A mixture of 3-iodophenol (3.0 mmol), 1-methylimidazole (4.5 mmol), Pd(OAc)₂ (5 mg, 0.01 mmol), KI (1.0 g, 6 mmol), and CuI (1.2 g, 6.1 mmol) in degassed DMF (12 mL) was heated under Ar at 140° C. for 5 days. After cooling to room temperature, the mixture was poured into NH₃ solution (10%, 50 mL), and CH₂Cl₂ (40×3 mL) was added. The organic phase was separated and dried (MgSO₄), and the solvent was evaporated. The crude product was purified by chromatograph (silica gel; hexanes-Et₂O, 4:1) to give MIz-Ph-OH as a light yellow solid (50%).

Synthesis of DMPz-Ph-O-Ph-MIz

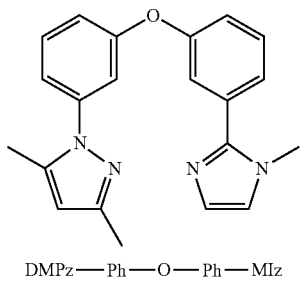

DMPz—Ph—O—Ph—MIz

After standard cycles of evacuation and back-fill with dry and pure nitrogen, an oven-dried Schlenk flask equipped with a magnetic stir bar was charged with Cu₂O (0.1 mmol, 10 mol %), DMPz-Ph-OH (1.0 mmol), K₂CO₃ (2.5 mmol), DMPz-Ph-I (1.0 mmol), and anhydrous and degassed DMAc (20 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product (DMPz-Ph)₂-O in 70% yield. $^1$H NMR (CDCl₃, 500 MHz): δ 2.27 (s, 3H), 2.30 (s, 3H), 3.75 (s, 3H), 5.98 (s, 1H), 6.96 (d, 1H), 7.00 (dd, 1H), 7.07-7.10 (m, 2H), 7.14 (dd, 1H), 7.18 (dd, 1H), 7.32 (d, 1H), 7.37-7.45 (m, 3H).

Synthesis of [DMPz-Ph-O-Ph-MIz]Pt (II)

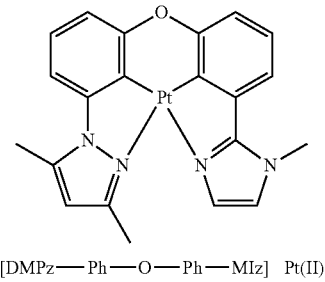

[DMPz—Ph—O—Ph—MIz] Pt(II)

A mixture of DMPz-Ph-O-Ph-MIz (1 mmol), K₂PtCl₄ (0.41 mg, 1 mmol), and acetic acid (10 mL) was refluxed for 3 days. The mixture was allowed to cool to room temperature. The resulting yellow complex was filtered off and washed with MeOH, H₂O, EtOH, and Et₂O, and dried under vacuum to produce [DMPz-Ph-O-Ph-MIz]Pt (II) in 80% yield. The product was purified by recrystallization from dimethyl sulfoxidee/methanol for further testing. $^1$H NMR (CDCl₃, 500 MHz): δ 2.65 (s, 3H), 2.72 (s, 3H), 4.08 (s, 3H), 6.41 (s, 1H), 6.88 (d, 1H), 6.99 (s, 1H), 7.12-7.19 (m, 2H), 7.24 (d, 1H), 7.43-7.47 (m, 3H).

Synthesis of [MPz-Py-O-Ph-O-Py]Pt (II)

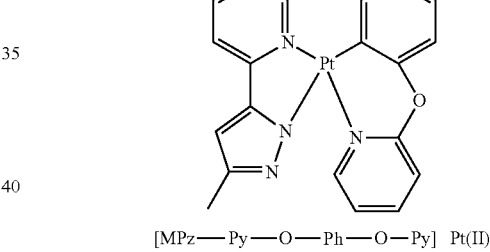

[MPz—Py—O—Ph—O—Py] Pt(II)

A mixture of MPz-Py-O-Ph-O-Py (1 mmol), K₂PtCl₄ (1 mmol), and acetic acid (20 mL) was refluxed for 3 days. The mixture was allowed to cool to room temperature. The resulting yellow complex was filtered off and washed with MeOH, H₂O, EtOH, and Et₂O, and dried under vacuum to produce [MPz-Py-O-Ph-O-Py]Pt (II) in 50% yield. $^1$H NMR (D₆-DMSO, 500 MHz): δ2.43 (s,3H), 7.08 (d,1H), 7.13-7.16 (m, 2H), 7.30 (t, 1H), 7.43 (t, 1H), 7.50 (d, 1H), 7.60 (d, 1H), 8.04 (d, 1H), 8.30 (t, 1H), 8.35 (t, 1H), 9.12 (d, 1H).

Example 3

Preparation of Specific Aspect [Py-O-Ph-O-Py-dMPz]Pt (Pt001)

Synthesis of Py-O-Ph-OH

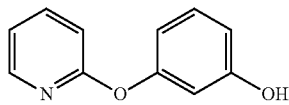 [SMILES: Oc1cccc(Oc2ccccn2)c1]

Under a nitrogen atmosphere, a pressure vessel was charged with a magnetic stir bar, resorcinol (110 mmol), 2-bromopyridine (100 mmol), 1-methylimidazole (5 mmol), and potassium carbonate (200 mmol). Pyridine (80 mL) was added and bubbled with nitrogen for 20 minutes before copper(I) iodide (10 mmol) was added and bubbled 10 minutes further. The vessel was sealed and heated to 140° C. while stirring. After 2 days, the solution was allowed to cool. The solids were filtered off and rinsed with a 50:50 mixture of toluene and methanol. The filtrate was reduced by rotoevaporation and 150 ml of water containing 10 mL glacial acetic acid was added and shaken vigorously. The water was decanted off and 50 mL of dichloromethane was added, forming an off white precipitate which was collected by vacuum filtration and dried with ether, resulting in the pure product Py-O-Ph-OH with a 55% yield. $^1$H NMR (CDCl$_3$): 5.98 (s, 1H), 6.59 (s, 1H), 6.62-6.69 (m, 2H), 6.94 (d, 1H), f7.02 (dd, 1H), 7.23 (vt, 1H), 7.70 (dd, 1H), 8.23 (b, 1H).

Synthesis of Py-O-Ph-O-Ph-Br

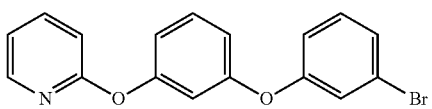 [SMILES: Brc1cccc(Oc2cccc(Oc3ccccn3)c2)c1]

Under a nitrogen atmosphere, a pressure vessel was charged with a magnetic stir bar, Py-O-Ph-OH (50 mmol), 2,6-dibromopyridine (50 mmol), 1-methylimidazole (25 mmol), and potassium carbonate (100 mmol). Toluene (80 mL) was added and bubbled with nitrogen for 20 minutes before copper(I) iodide (5 mmol) was added and the solution bubbled for 10 minutes further. The vessel was sealed and heated to 140° C. while stirring. After 2 days, the solution was allowed to cool and the solids were filtered off and rinsed with dichloromethane. The filtrate was added to a separatory funnel containing dichloromethane and water. The water phase was washed 3 times with 75 mL dichloromethane, and the combined organic layers were washed once with pure water. The organic layer was collected, dried with magnesium sulfate, filtered, and the filtrate reduced by rotoevaporation. The resulting oil was purified by column chromatography using dichloromethane over silica resulting in the pure product Py-O-Ph-O-Ph-Br with a 60% yield. $^1$H NMR (CDCl$_3$): 6.80-6.85 (m, 2H), 6.91 (s, 1H), 6.94 (s, 1H), 6.97-7.03 (m, 2H), 7.19 (vt, 1H), 7.21-7.24 (m, 2H), 7.36 (vt, 1H), 7.70(dd, 1H), 8.21(dd, 1H).

Synthesis of Py-O-Ph-O-Ph-dMPz

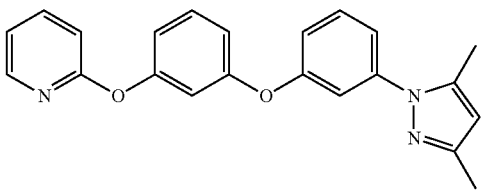 [SMILES: Cc1cc(C)n(-c2cccc(Oc3cccc(Oc4ccccn4)c3)c2)n1]

After standard cycles of evacuation and back-fill with dry and pure nitrogen, an oven-dried Schlenk flask equipped with a magnetic stir bar was charged with Cu$_2$O (1 mmol, 10 mol %), syn-2-pyridinealdoxime (4 mmol, 20 mol %), 3,5-dimethylpyrazole (12 mmol), Cs$_2$CO$_3$ (25 mmol), Py-O-Ph-O-Ph-Br (10 mmol), and anhydrous, degassed acetonitrile (100 mL). The solution was refluxed for 2 days, allowed to cool to room temperature, diluted with dichloromethane, and filtered through a plug of Celite. The filter cake was washed with dichloromethane (100 mL) and the filtrate was concentrated under vacuo to yield a residue, which was purified by column chromatography on silica gel to obtain the pure product Py-O-Ph-O-Ph-dMPz in 45% yield. $^1$H NMR (CDCl$_3$): 2.29 (s, 3H), 2.28 (s, 3H), 5.98 (s, 1H), 6.84 (vt, 1H), 6.85-6.93 (m, 3H), 6.98-7.04 (m, 2H), 7.13 (vt, 1H), 7.19 (dd, 1H), 7.35 (vt, 1H), 7.39 (vt, 1H), 7.69 (dd, 1H), 8.19 (dd, 1H).

Synthesis of [Py-O-Ph-O-Ph-dMPz]Pt (Pt001)

A mixture of Py-O-Ph-O-Ph-dMPz (1 mmol), K$_2$PtCl$_4$ (0.41 mg, 1 mmol), and acetic acid (35 mL) was refluxed for 3 days. The mixture was allowed to cool to room temperature. The resulting white complex was filtered off and washed with H$_2$O, MeOH, and Et$_2$O, and dried under vacuum to produce [Py-O-Ph-O-Ph-dMPz]Pt in 60% yield. $^1$H NMR (CDCl$_3$): 2.23 (s, 3H), 2.70 (s, 3H), 6.09 (s, 1H), 6.93 (dd, 1H), 7.01 (vt, 1H), 7.03-7.11 (m, 3H), 7.14 (d, 1H), 7.17 (vt, 1H), 7.37 (d, 1H), 7.88 (dd, 1H), 8.80 (d, 1H).

The compound was sublimed under vacuum over a four zone gradient of 220° C.-190° C.-150° C.-110° C. and collected with a 65% yield.

Figure 4:
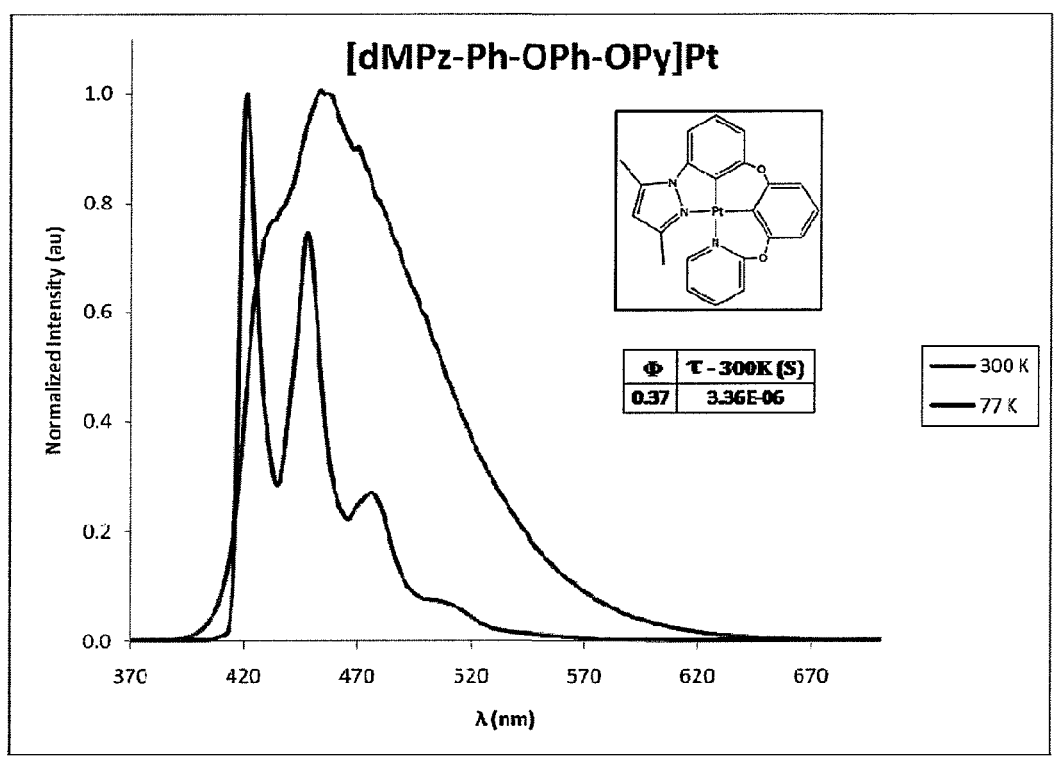
FIG. 4 is a photoluminescence spectrum produced from a specific aspect, [dMPz-Ph-O-Ph-O-Py]Pt taken at 77 K and 300 K.

A photoluminescence spectrum of [Py-O-Ph-O-Py-dMPz]Pt at 77 K and 300 K is illustrated in FIG. 4.

Example 4

Preparation of Specific Aspect [Py-O-Ph-O-Ph-MIz]Pt (Pt002)

Synthesis of Py-O-Ph-O-Ph-MIz

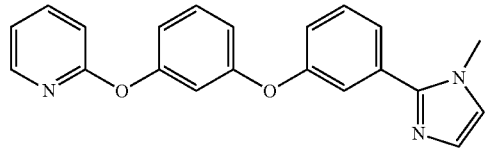 [SMILES: Cn1ccnc1-c1cccc(Oc2cccc(Oc3ccccn3)c2)c1]

Under a nitrogen atmosphere, a 35 mL microwave vial was charged with a magnetic stir bar, Py-O-Ph-O-Ph-Br (10 mmol), copper(I) iodide (20 mmol), and 1-methylimidazole (11 mmol). DMF (15 mL) was added and bubbled with nitrogen for 20 minutes before palladium acetate (0.5 mmol) was added and the solution further bubbled for 10 minutes. The vial was sealed and irradiated while stirring at 150 W, 155° C. for 2 hours. The solution was allowed to cool, dumped into a stirring mixture of 100 mL of dichloromethane (DCM) and 150 mL of a 15% aqueous solution of NH$_4$OH for 30 minutes, and poured into a separatory funnel. The organic layer was separated and the aqueous layer was washed twice more with DCM (50 mL). The organic layers were combined and washed once with pure water (50 mL). The organic layer was dried with magnesium sulfate, filtered, and reduced by rotoevaporation. The resulting oil was purified by column chromatography using DCM and methanol over silica resulting in the pure product Py-O-Ph-O-Ph-MIz in an 80% yield. $^1$H NMR (CDCl$_3$): 3.73 (s, 3H) 6.83 (vt, 1H), 6.84-6.93 (m, 3H), 6.96 (d, 1H), 7.00 (dd, 1H), 7.08-7.13 (m, 2H), 7.31 (d, 1H), 7.34 (vt, 1H), 7.41 (d, 1H), 7.42 (vt, 1H), 7.68 (dd, 1H), 8.19 (dd, 1H).

Synthesis of [Py-O-Ph-O-Ph-MIz]Pt (Pt002)

A mixture of Py-O-Ph-O-Ph-MIz (1 mmol), K$_2$PtCl$_4$ (0.41 mg, 1 mmol), and acetic acid (35 mL) was refluxed for 3 days. The mixture was allowed to cool to room temperature. The resulting white complex was filtered off and washed with H$_2$O, MeOH, and Et$_2$O, and dried under vacuum to produce

[Py-O-Ph-O-Ph-MIz]Pt in 60% yield. ¹H NMR (CDCl₃): 4.02 (s, 3H), 6.87-6.93 (m, 2H), 7.01 (d, 1H), 7.05-7.13 (m, 4H), 7.17 (vt, 1H), 7.27 (d, 1H), 7.32 (d, 1H), 7.90 (dd, 1H), 8.81 (dd, 1H).

The compound was sublimed under vacuum over a four zone gradient of 220° C.-190° C.-160° C.-130° C. and collected with a 60% yield.

Figure 5:
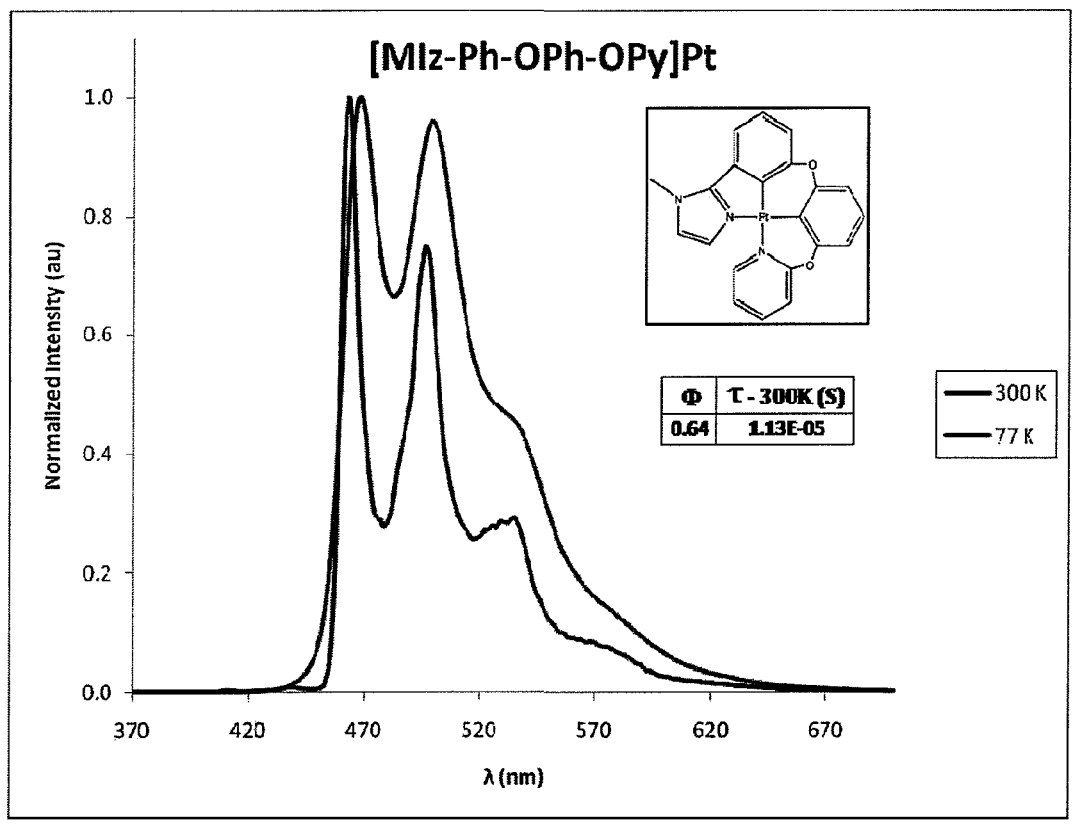
FIG. 5 is a photoluminescence spectrum produced from a specific aspect, [MIz-Ph-O-Ph-O-Py]Pt taken at 77 K and 300 K.

A photoluminescence spectrum of [Py-O-Ph-O-Ph-MIz]Pt at 77 K and 300 K is illustrated in FIG. 5.

Figure 6:
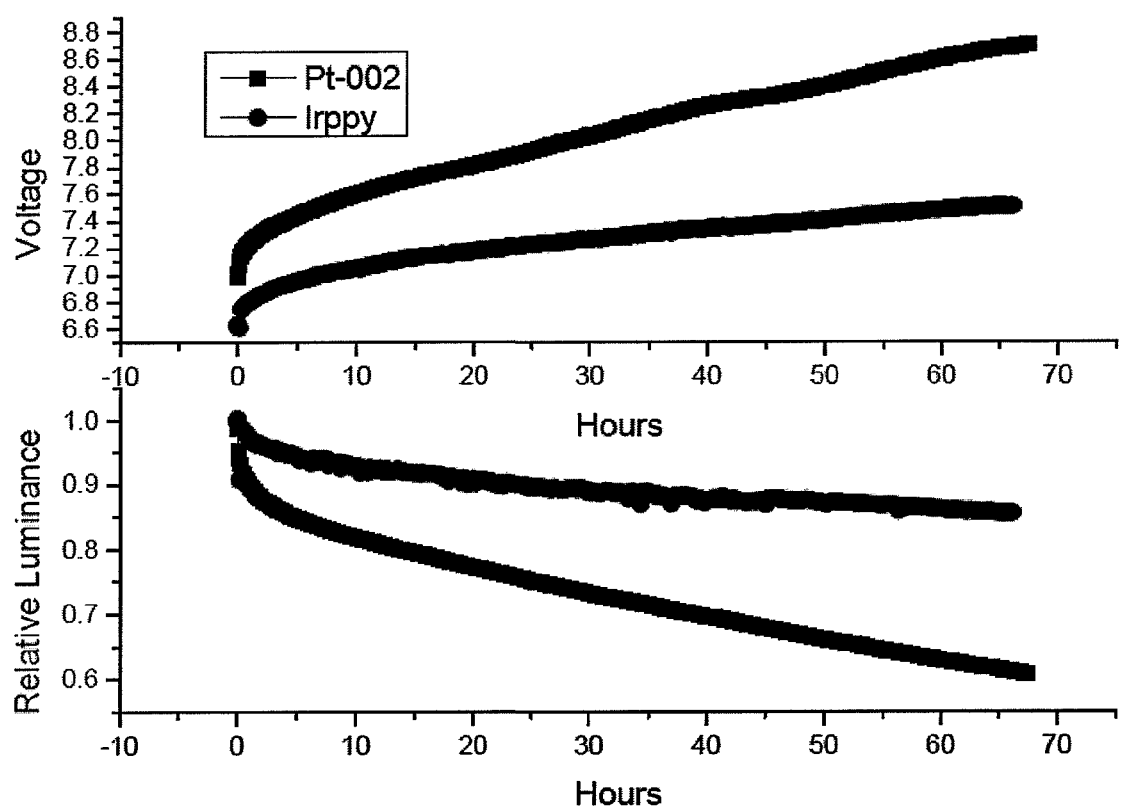
FIG. 6 is a plot of voltage (top) and luminance (bottom) vs. time for an Ir(ppy)$_3$ and Pt002 device.

FIG. 6 illustrates a plot of voltage (top) and luminance (bottom) vs. time for an Ir(ppy)₃ and Pt002 device. The general device structure is ITO/CuPc(10 nm)/NPD(30 nm)/25 nm EML(Ir(ppy)₃ (6%):CBP or Pt002(2%):CBP)/BAlq(10 nm)/Alq(30 nm)/LiF(1 nm)/Al(100 nm). The device were driven at constant current of 2 mA/cm².

Example 5

Preparation of Specific Aspect [Py-O-Ph-O-Ph-Py]Pt (Pt003)

Synthesis of Py-O-Ph-O-Ph-Py

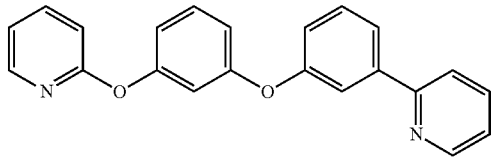 [SMILES: c1ccc(Oc2cccc(Oc3cccc(-c4ccccn4)c3)c2)nc1]

Under a nitrogen atmosphere, an oven dried three neck flask was charged with a magnetic stir bar, Py-O-Ph-O-Ph-Br (10 mmol), and 2-(tripropylstannyl)pyridine (10 mmol). Dry toluene (100 mL) was added and bubbled with nitrogen for 20 minutes before Tetrakis(triphenylphosphine)palladium(0) (0.5 mmol) was added, bubbled 10 minutes further, and brought to reflux for 2 days. After cooling, the contents of the flask were filtered, the liquid reduced by rotoevaporation, and the resulting oil was purified by column chromatography using DCM over silica to yield the pure product Py-O-Ph-O-Ph-Py with a 65% yield. ¹H NMR (CDCl₃): 6.84 (vt, 1H), 6.85-6.89 (m, 2H), 6.91(d, 1H), 6.98 (dd, 1H), 7.11 (dd, 1H), 7.24 (dd, 1H), 7.34(vt, 1H), 7.44 (vt, 1H), 7.66-7.78 (m, 5H), 8.19 (dd, 1H), 8.67 (dd, 1H).

Synthesis of [Py-O-Ph-O-Ph-Py]Pt (Pt003)

A mixture of Py-O-Ph-O-Ph-Py (1 mmol), K₂PtCl₄ (0.41 mg, 1 mmol), and acetic acid (35 mL) was refluxed for 3 days. The mixture was allowed to cool to room temperature. The resulting white complex was filtered off and washed with H₂O, MeOH, and Et₂O, and dried under vacuum to produce [Py-O-Ph-O-Ph-Py]Pt in 60% yield. ¹H NMR (CDCl₃): 6.95 (dd, 1H), 7.12 (d, 1H), 7.13 (s, 1H), 7.17-7.25 (m, 4H), 7.40 (d, 1H), 7.50 (d, 1H), 7.87-7.97 (m, 3H), 8.47 (d, 1H), 8.63 (d, 1H).

The compound was sublimed under vacuum over a four zone gradient of 185° C.-150° C.-130° C.-100° C. and collected with a 70% yield.

Figure 7:
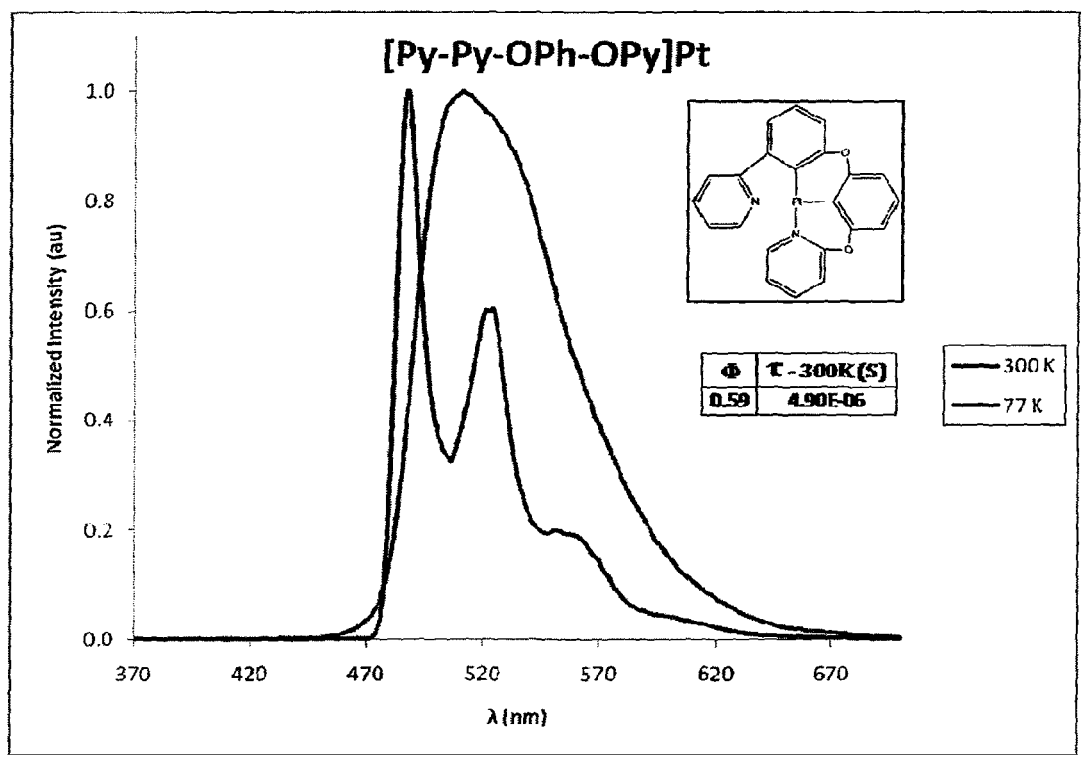
FIG. 7 is a photoluminescence spectrum produced from a specific aspect, [Py-Py-O-Ph-O-Py]Pt taken at 77 K and 300K.

A photoluminescence spectrum of [Py-O-Ph-O-Ph-Py]Pt at 77 K and 300 K is illustrated in FIG. 7.

Example 6

Preparation of Specific Aspect [Py-O-Ph-O-Py-MPz]Pt (Pt004)

Synthesis of Py-O-Ph-O-Py-EA

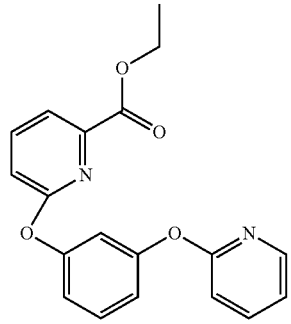 [SMILES: CCOC(=O)c1cccc(Oc2cccc(Oc3ccccn3)c2)n1]

Under a nitrogen atmosphere, a pressure vessel was charged with a magnetic stir bar, Py-O-Ph-OH (20 mmol), Ethyl 6-bromo-2-pyridinecarboxylate (20 mmol), 1-methylimidazole (10 mmol), and potassium carbonate (40 mmol). Dry toluene (70 mL) was added and bubbled with nitrogen for 20 minutes before copper(I) iodide (2 mmol) was added and bubbled for 10 minutes further. The vessel was sealed, and heated to 140° C. oil while stirring. After 2 days, the solution was allowed to cool and the solids were filtered off and rinsed with dichloromethane. The filtrate was added to a separatory funnel containing DCM and water. The water phase was washed 3 times with 75 mL DCM, and the combined organic layers were washed once with pure water. The organic layer was collected, dried with magnesium sulfate, filtered, and the filtrate reduced by rotoevaporation. The resulting oil was purified by column chromatography using DCM over silica resulting in the pure product Py-O-Ph-O-Py-EA with a 45% yield. ¹H NMR (CDCl₃): 1.38 (s, 3H), 4.41 (q, 2H), 6.94 (d, 1H), 6.98-7.05 (m, 5H), 7.41 (vt, 1H), 7.69 (dd, 1H), 7.77-7.87 (m, 2H), 8.21 (d, 1H).

Synthesis of Py-O-Ph-O-Py-diKeytone

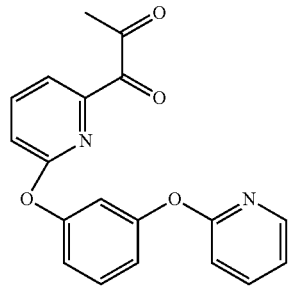 [SMILES: CC(=O)C(=O)c1cccc(Oc2cccc(Oc3ccccn3)c2)n1]

Under a nitrogen atmosphere, an oven dried three neck flask was charged with a magnetic stir bar, sodium methoxide (13 mmol) and dry THF (100 mL). The solution was bubbled with nitrogen for 20 minutes and placed in an ice bath. Dry acetone (11 mmol) was slowly added. After 10 minutes of stirring, Py-O-Ph-O-Py-EA (10 mmol) dissolved in a small amount of dry THF was added. The solution was stirred under nitrogen for 3 hours, brought to room temperature, and refluxed for 3 hours further.

After cooling, 100 mL of DCM with 10 mL of acetic acid was added to the vessel. The solids were filtered off and washed with DCM. The filtrate was collected, reduced by rotoevaporation, and the resulting oil subjected to column chromatography with DCM over silica resulting in the pure product Py-O-Ph-O-PydiKeytone in a 50% yield. $^1$H NMR (CDCl$_3$): 2.15 (s, 3H), 6.60 (s, 1H), 6.94 (d, 1H), 7.00-7.05 (m, 5H), 7.43 (dd, 1H), 7.70 (dd, 1H), 7.81 (s, 4H), 7.82 (d, 1H), 8.21 (d, 1H).

Synthesis of Py-O-Ph-O-Py-MPz

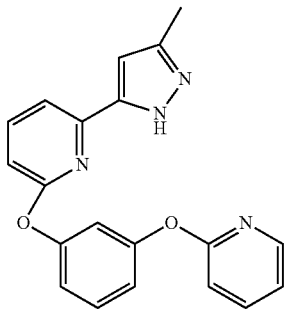 [SMILES: Cc1cc(-c2cccc(Oc3cccc(Oc4ccccn4)c3)n2)[nH]n1]

A round bottom flask was charged with a magnetic stir bar, Py-O-Ph-O-Py-diKeytone (10 mmol), and hydrazine (12 mmol) in a 40% solution with water. Ethanol (50 mL) was added and refluxed for 2 hours while stirring under nitrogen and allowed to cool. The cooled solution was dumped into 150 mL of brine which was extracted 3 times with DCM. The combined extractions were dried with magnesium sulfate, filtered, and reduced by rotoevaporation. The resulting oil was subjected to a flash column with DCM over silica giving Py-O-Ph-O-Py-MPz with a 70% yield. $^1$H NMR (CDCl$_3$): 2.30 (s, 3H), 5.28 (s, 0.6H), 6.45 (s, 1H), 6.82 (d, 1H), 6.94 (d, 1H), 6.96-7.02 (m, 4H), 7.33 (d, 1H), 7.42 (vt, 1H), 7.67 (q, .4H), 7.68-7.73 (m, 2H), 8.25 (dd, 1H).

Synthesis of [Py-O-Ph-O-Py-MPz]Pt (Pt004)

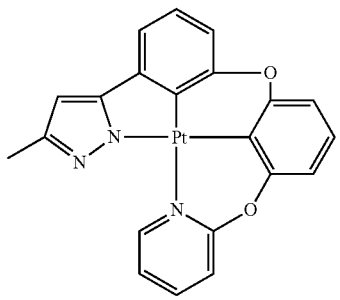

A mixture of Py-O-Ph-O-Py-MPz (1 mmol), K$_2$PtCl$_4$ (0.41 mg, 1 mmol), and acetic acid (35 mL) was refluxed for 3 days. The mixture was allowed to cool to room temperature. The resulting white complex was filtered off and washed with H$_2$O, MeOH, and Et$_2$O, and dried under vacuum to produce [Py-O-Ph-O-Py-MPz]Pt in 80% yield.

Figure 8:
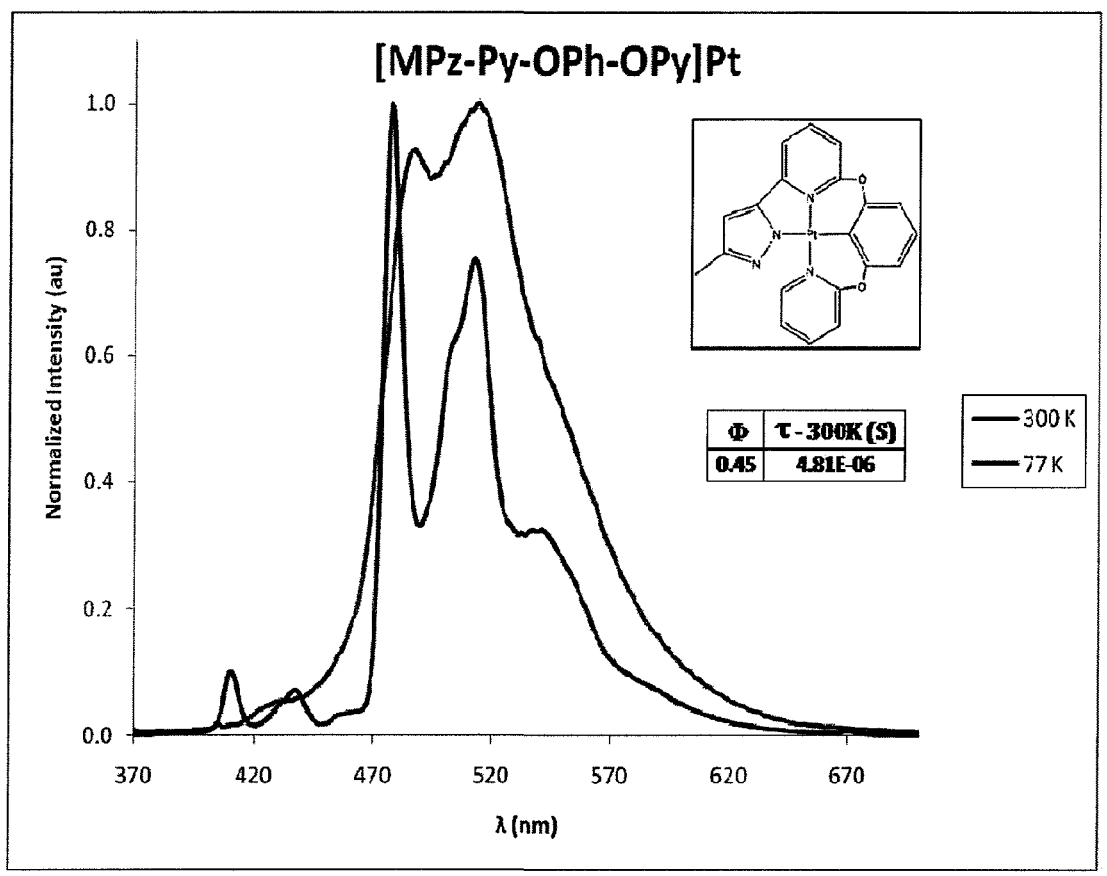
FIG. 8 is a photoluminescence spectrum produced from a specific aspect, [MPz-Py-O-Ph-O-Py]Pt taken at 77 K and 300 K.

A photoluminescence spectrum of [Py-O-Ph-O-Py-MPz] Pt at 77 K and 300 K is illustrated in FIG. 8.

What is claimed is:

1. A compound represented by one of the following formulas:

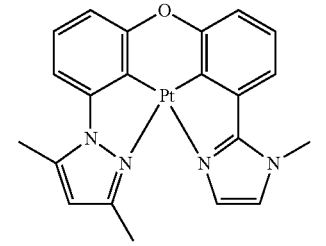

[DMPz—Ph—O—Ph—MIz] Pt(II),

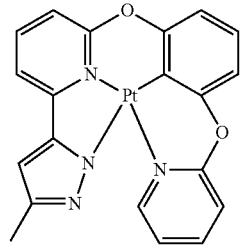

[MPz—Py—O—Ph—O—Py] Pt(II),

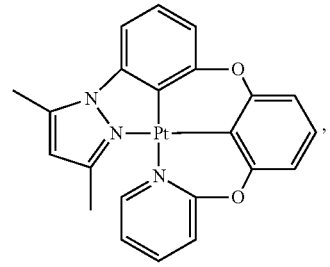

,

, or

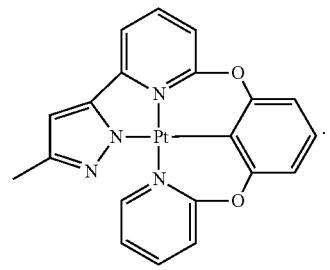

.

2. The compound of claim 1, represented by the formula:
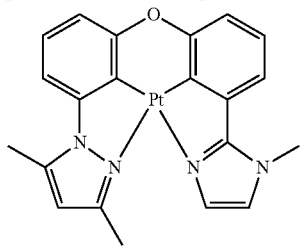
[DMPz—Ph—O—Ph—MIz] Pt(II).
3. The compound of claim 1, represented by the formula:
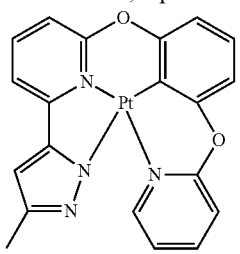
[MPz—Py—O—Ph—O—Py] Pt(II).
4. The compound of claim 1, represented by the formula:
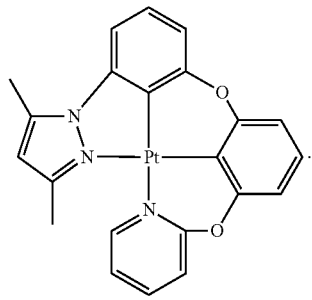
5. The compound of claim 1, represented by the formula:
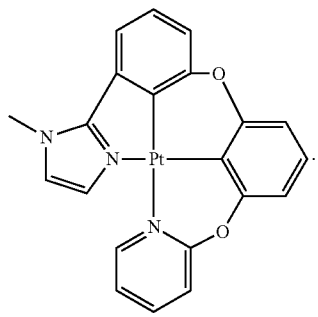
6. The compound of claim 1, represented by the formula:
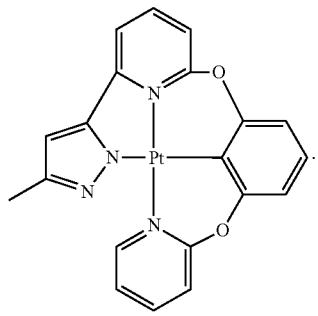
* * * * *